US012667694B2

(12) United States Patent
Lindekugel et al.

(10) Patent No.: US 12,667,694 B2
(45) Date of Patent: Jun. 30, 2026

(54) GUIDEWIRE STABILIZATION SYSTEM FOR RAPIDLY INSERTED CENTRAL CATHETER (RICC) PLACEMENT SYSTEM

(71) Applicant: Bard Access Systems, Inc., Salt Lake City, UT (US)

(72) Inventors: Eric W. Lindekugel, Salt Lake City, UT (US); Daniel B. Blanchard, Bountiful, UT (US); Glade H. Howell, Draper, UT (US); Kyle G. Thornley, Farmington, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 746 days.

(21) Appl. No.: 17/970,005

(22) Filed: Oct. 20, 2022

(65) Prior Publication Data

US 2023/0128853 A1     Apr. 27, 2023

Related U.S. Application Data

(60) Provisional application No. 63/270,489, filed on Oct. 21, 2021.

(51) Int. Cl.
*A61M 25/01* (2006.01)
*A61M 5/158* (2006.01)
*A61M 25/00* (2006.01)

(52) U.S. Cl.
CPC ............ *A61M 25/01* (2013.01); *A61M 5/158* (2013.01); *A61M 25/0097* (2013.01)

(58) Field of Classification Search
CPC .............. A61M 5/158; A61M 25/0606; A61M 2025/09116; A61M 2025/09125;
(Continued)

(56) References Cited

U.S. PATENT DOCUMENTS

| | | | |
|---|---|---|---|
| 1,013,691 A | 1/1912 | Shields | |
| 3,225,762 A | 12/1965 | Guttman | |

(Continued)

FOREIGN PATENT DOCUMENTS

| | | | | |
|---|---|---|---|---|
| CA | 3038151 A1 * | 11/2018 | ........ | A61M 25/0097 |
| CN | 202526749 U | 11/2012 | | |

(Continued)

OTHER PUBLICATIONS

PCT/US2022/047252 filed Oct. 20, 2022 International Search Report and Written Opinion dated Mar. 21, 2023.
(Continued)

*Primary Examiner* — Cris L. Rodriguez
(74) *Attorney, Agent, or Firm* — Rutan & Tucker LLP

(57) ABSTRACT

A guidewire stabilization mechanism for a catheter placement system can include an actuator button that can be actuated by the user to grip the guidewire in a locked position. With the guidewire locked relative to a housing of the stabilization mechanism a user can detach a needle hub from the housing and withdraw the needle proximally. A portion of the guidewire can pass through a needle slot to disengage the needle from the guidewire. The stabilization mechanism can prevent the guidewire from being dislodged from the vasculature as the needle is withdrawn. The stabilization mechanism can be biased towards the unlocked position, towards the locked position, can be bistable in both the locked and unlocked positions, or can be activated by the removal of the needle.

25 Claims, 14 Drawing Sheets

(58) Field of Classification Search
CPC .......... A61M 25/0105; A61M 25/0612; A61M
25/065; A61M 39/02; A61M 2039/0202;
A61M 25/0637; A61M 39/10; A61M
2025/0266; A61M 2025/028; A61M
25/0043; A61M 25/0017; A61M 25/0097;
A61M 2025/024; A61M 29/00; A61M
29/250631; A61M 25/09; A61M
2025/0687; A61M 2028/0681; A61M
2025/0656
See application file for complete search history.

(56) References Cited

U.S. PATENT DOCUMENTS

| | | | |
|---|---|---|---|
| 3,890,976 A | 6/1975 | Bazell et al. | |
| 4,051,849 A | 10/1977 | Poncy et al. | |
| 4,205,675 A | 6/1980 | Vaillancourt | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |
| 4,637,404 A | 1/1987 | Gessman | |
| 4,840,613 A | 6/1989 | Balbierz | |
| 4,935,008 A | 6/1990 | Lewis, Jr. | |
| 4,995,872 A | 2/1991 | Ferrara | |
| 5,017,259 A | 5/1991 | Kohsai | |
| 5,040,548 A | 8/1991 | Yock | |
| 5,057,073 A | 10/1991 | Martin | |
| 5,059,183 A | 10/1991 | Semrad | |
| 5,112,312 A | 5/1992 | Luther | |
| 5,120,317 A | 6/1992 | Luther | |
| 5,188,593 A | 2/1993 | Martin | |
| 5,195,962 A | 3/1993 | Martin et al. | |
| 5,207,650 A | 5/1993 | Martin | |
| 5,219,332 A | 6/1993 | Nelson et al. | |
| 5,263,938 A | 11/1993 | Orr et al. | |
| 5,267,958 A | 12/1993 | Buchbinder et al. | |
| 5,273,042 A | 12/1993 | Lynch et al. | |
| 5,273,052 A | 12/1993 | Kraus et al. | |
| 5,282,479 A | 2/1994 | Havran | |
| 5,295,970 A | 3/1994 | Clinton et al. | |
| 5,306,247 A | 4/1994 | Pfenninger | |
| 5,328,472 A | 7/1994 | Steinke et al. | |
| 5,350,358 A | 9/1994 | Martin | |
| 5,363,847 A | 11/1994 | Viera | |
| 5,368,567 A | 11/1994 | Lee | |
| 5,378,230 A | 1/1995 | Mahurkar | |
| 5,380,290 A | 1/1995 | Makower et al. | |
| 5,380,307 A | 1/1995 | Chee et al. | |
| 5,389,087 A | 2/1995 | Miraki | |
| 5,397,310 A * | 3/1995 | Chu .................. A61M 39/0613 |
| | | | 604/167.03 |
| 5,415,177 A | 5/1995 | Zadini et al. | |
| 5,420,882 A | 5/1995 | Black | |
| 5,439,449 A | 8/1995 | Mapes et al. | |
| 5,443,457 A | 8/1995 | Ginn et al. | |
| 5,489,271 A | 2/1996 | Andersen | |
| 5,573,520 A | 11/1996 | Schwartz et al. | |
| 5,683,370 A | 11/1997 | Luther et al. | |
| 5,718,678 A | 2/1998 | Fleming, III | |
| 5,772,636 A | 6/1998 | Brimhall et al. | |
| 5,827,202 A | 10/1998 | Miraki et al. | |
| 5,885,251 A | 3/1999 | Luther | |
| 5,919,164 A | 7/1999 | Andersen | |
| 5,947,940 A | 9/1999 | Beisel | |
| 5,957,893 A | 9/1999 | Luther et al. | |
| 6,123,084 A | 9/2000 | Jandak et al. | |
| 6,206,849 B1 | 3/2001 | Martin et al. | |
| 6,228,062 B1 | 5/2001 | Howell et al. | |
| 6,475,187 B1 | 11/2002 | Gerberding | |
| 6,606,515 B1 | 8/2003 | Windheuser et al. | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |

| | | | |
|---|---|---|---|
| 6,926,692 B2 | 8/2005 | Katoh et al. | |
| 6,962,575 B2 | 11/2005 | Tal | |
| 6,994,693 B2 | 2/2006 | Tal | |
| 6,999,809 B2 | 2/2006 | Currier et al. | |
| 7,025,746 B2 | 4/2006 | Tal | |
| 7,029,467 B2 | 4/2006 | Currier et al. | |
| 7,037,293 B2 | 5/2006 | Carrillo et al. | |
| 7,074,231 B2 | 7/2006 | Jang | |
| 7,141,050 B2 | 11/2006 | Deal et al. | |
| 7,144,386 B2 | 12/2006 | Korkor et al. | |
| 7,311,697 B2 | 12/2007 | Osborne | |
| 7,364,566 B2 | 4/2008 | Elkins et al. | |
| 7,377,910 B2 | 5/2008 | Katoh et al. | |
| 7,390,323 B2 | 6/2008 | Jang | |
| D600,793 S | 9/2009 | Bierman et al. | |
| D601,242 S | 9/2009 | Bierman et al. | |
| D601,243 S | 9/2009 | Bierman et al. | |
| 7,594,911 B2 | 9/2009 | Powers et al. | |
| 7,691,093 B2 | 4/2010 | Brimhall | |
| 7,722,567 B2 | 5/2010 | Tal | |
| D617,893 S | 6/2010 | Bierman et al. | |
| D624,643 S | 9/2010 | Bierman et al. | |
| 7,819,889 B2 | 10/2010 | Healy et al. | |
| 7,857,770 B2 | 12/2010 | Raulerson et al. | |
| 7,857,788 B2 | 12/2010 | Racz | |
| D630,729 S | 1/2011 | Bierman et al. | |
| 7,909,797 B2 | 3/2011 | Kennedy, II et al. | |
| 7,909,811 B2 | 3/2011 | Agro et al. | |
| 7,922,696 B2 | 4/2011 | Tal et al. | |
| 7,938,820 B2 | 5/2011 | Webster et al. | |
| 7,967,834 B2 | 6/2011 | Tal et al. | |
| 7,985,204 B2 | 7/2011 | Katoh et al. | |
| 8,073,517 B1 | 12/2011 | Burchman | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,206,356 B2 | 6/2012 | Katoh et al. | |
| 8,372,107 B2 | 2/2013 | Tupper | |
| 8,377,006 B2 | 2/2013 | Tal et al. | |
| 8,454,577 B2 | 6/2013 | Joergensen et al. | |
| 8,585,858 B2 | 11/2013 | Kronfeld et al. | |
| 8,652,119 B2 | 2/2014 | Nishigishi | |
| 8,657,790 B2 | 2/2014 | Tal et al. | |
| 8,672,888 B2 | 3/2014 | Tal | |
| 8,696,645 B2 | 4/2014 | Tal et al. | |
| 8,784,362 B2 | 7/2014 | Boutilette et al. | |
| 8,827,958 B2 | 9/2014 | Bierman et al. | |
| 8,876,704 B2 | 11/2014 | Golden et al. | |
| 8,882,713 B1 | 11/2014 | Call et al. | |
| 8,900,192 B2 | 12/2014 | Anderson et al. | |
| 8,900,207 B2 | 12/2014 | Uretsky | |
| 8,915,884 B2 | 12/2014 | Tal et al. | |
| 8,956,327 B2 | 2/2015 | Bierman et al. | |
| 9,023,093 B2 | 5/2015 | Pal | |
| 9,095,683 B2 * | 8/2015 | Hall .................... A61M 29/00 |
| 9,138,252 B2 | 9/2015 | Bierman et al. | |
| 9,180,275 B2 | 11/2015 | Helm | |
| 9,265,920 B2 | 2/2016 | Rundquist et al. | |
| 9,272,121 B2 | 3/2016 | Piccagli | |
| 9,522,254 B2 | 12/2016 | Belson | |
| 9,554,785 B2 | 1/2017 | Walters et al. | |
| 9,566,087 B2 | 2/2017 | Bierman et al. | |
| 9,579,484 B2 | 2/2017 | Barnell | |
| 9,675,784 B2 | 6/2017 | Belson | |
| 9,713,695 B2 | 7/2017 | Bunch et al. | |
| 9,764,117 B2 | 9/2017 | Bierman et al. | |
| 9,770,573 B2 | 9/2017 | Golden et al. | |
| 9,814,861 B2 | 11/2017 | Boutillette et al. | |
| 9,820,845 B2 | 11/2017 | von Lehe et al. | |
| 9,861,383 B2 | 1/2018 | Clark | |
| 9,884,169 B2 | 2/2018 | Bierman et al. | |
| 9,889,275 B2 | 2/2018 | Voss et al. | |
| 9,913,585 B2 | 3/2018 | McCaffrey et al. | |
| 9,913,962 B2 | 3/2018 | Tal et al. | |
| 9,981,113 B2 | 5/2018 | Bierman | |
| 10,010,312 B2 | 7/2018 | Tegels | |
| 10,065,020 B2 | 9/2018 | Gaur | |
| 10,098,724 B2 | 10/2018 | Adams et al. | |
| 10,111,683 B2 | 10/2018 | Tsamir et al. | |

(56)     References Cited

U.S. PATENT DOCUMENTS

| | | | |
|---|---|---|---|
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 11,285,301 B2 | 3/2022 | Ornelas Vargas et al. |
| 11,400,261 B2 | 8/2022 | Mathews et al. |
| 2002/0040231 A1 | 4/2002 | Wysoki |
| 2002/0072712 A1* | 6/2002 | Nool ................ A61M 25/0136 |
| | | 604/164.08 |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0116901 A1 | 6/2004 | Appling |
| 2004/0167443 A1 | 8/2004 | Shireman et al. |
| 2004/0193093 A1 | 9/2004 | Desmond |
| 2004/0225232 A1 | 11/2004 | Malmborg et al. |
| 2004/0230178 A1 | 11/2004 | Wu |
| 2005/0004554 A1 | 1/2005 | Osborne |
| 2005/0245847 A1 | 11/2005 | Schaeffer |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0064036 A1 | 3/2006 | Osborne et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0058839 A1 | 3/2008 | Nobles et al. |
| 2008/0091137 A1 | 4/2008 | Reavill |
| 2008/0097386 A1* | 4/2008 | Osypka ............. A61M 25/0668 |
| | | 604/167.03 |
| 2008/0125744 A1 | 5/2008 | Treacy |
| 2008/0125748 A1 | 5/2008 | Patel |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2009/0105653 A1 | 4/2009 | Spenser et al. |
| 2009/0187147 A1 | 7/2009 | Kurth et al. |
| 2009/0221961 A1 | 9/2009 | Tal et al. |
| 2009/0227900 A1 | 9/2009 | Kim et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0106057 A1 | 5/2011 | Hamboly |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0004665 A1 | 1/2012 | Defossez et al. |
| 2012/0041371 A1 | 2/2012 | Tal et al. |
| 2012/0065590 A1 | 3/2012 | Bierman et al. |
| 2012/0071857 A1 | 3/2012 | Goldfarb et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0304030 A1 | 11/2013 | Gray et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0045695 A1 | 2/2015 | Simpson et al. |
| 2015/0080939 A1 | 3/2015 | Adams et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1* | 8/2015 | Blanchard ....... A61M 25/09041 |
| | | 604/164.08 |
| 2015/0283357 A1 | 10/2015 | Lampropoulos et al. |
| 2015/0290432 A1 | 10/2015 | Mathews et al. |
| 2015/0297867 A1 | 10/2015 | Howell et al. |
| 2015/0297868 A1 | 10/2015 | Tal et al. |
| 2015/0320969 A1 | 11/2015 | Haslinger et al. |
| 2015/0328434 A1 | 11/2015 | Gaur |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0074628 A1 | 3/2016 | Smith et al. |
| 2016/0082223 A1 | 3/2016 | Barnell |
| 2016/0114124 A1 | 4/2016 | Tal |
| 2016/0220786 A1 | 8/2016 | Mitchell et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0014599 A1 | 1/2017 | Crisman et al. |
| 2017/0035990 A1 | 2/2017 | Swift |
| 2017/0072165 A1 | 3/2017 | Lim et al. |
| 2017/0080189 A1 | 3/2017 | Tao et al. |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0126126 A1* | 5/2018 | Ornelas Vargas ......................... |
| | | A61M 25/09041 |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0296799 A1 | 10/2018 | Horst et al. |
| 2018/0296804 A1 | 10/2018 | Bierman |
| 2019/0015646 A1 | 1/2019 | Matlock et al. |
| 2019/0022354 A1 | 1/2019 | Khanicheh et al. |
| 2019/0046770 A1 | 2/2019 | Shields |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2020/0316346 A1* | 10/2020 | Burkholz ........ A61M 25/09041 |
| 2021/0069471 A1 | 3/2021 | Howell |
| 2021/0085927 A1 | 3/2021 | Howell |
| 2021/0121661 A1 | 4/2021 | Howell |
| 2021/0121667 A1 | 4/2021 | Howell |

(56) References Cited

U.S. PATENT DOCUMENTS

| | | | |
|---|---|---|---|
| 2021/0228843 A1* | 7/2021 | Howell | A61M 25/0668 |
| 2021/0307854 A1 | 10/2021 | Bernhard et al. | |
| 2021/0322729 A1 | 10/2021 | Howell | |
| 2021/0330941 A1 | 10/2021 | Howell et al. | |
| 2021/0330942 A1 | 10/2021 | Howell | |
| 2021/0361915 A1 | 11/2021 | Howell et al. | |
| 2021/0402149 A1 | 12/2021 | Howell | |
| 2021/0402153 A1 | 12/2021 | Howell et al. | |
| 2022/0001138 A1 | 1/2022 | Howell | |
| 2022/0032013 A1 | 2/2022 | Howell et al. | |
| 2022/0032014 A1* | 2/2022 | Howell | A61M 25/0631 |
| 2022/0047267 A1 | 2/2022 | Johnston et al. | |
| 2022/0168548 A1* | 6/2022 | Dong | A61M 5/158 |
| 2022/0176082 A1 | 6/2022 | Mckinnon et al. | |
| 2022/0193379 A1 | 6/2022 | Howell | |
| 2022/0225914 A1* | 7/2022 | Chen | A61M 25/09041 |
| 2022/0379104 A1* | 12/2022 | Blanchard | A61M 25/09041 |
| 2022/0387761 A1* | 12/2022 | Ishida | A61M 25/0097 |
| 2022/0409275 A1 | 12/2022 | Hoang et al. | |
| 2023/0103883 A1 | 4/2023 | Oppegard et al. | |
| 2023/0129318 A1 | 4/2023 | Lindekugel et al. | |
| 2023/0255661 A1* | 8/2023 | Howell | A61B 17/32093 |
| | | | 606/170 |
| 2023/0277812 A1 | 9/2023 | Howell et al. | |
| 2024/0374873 A1 | 11/2024 | Spataro et al. | |
| 2025/0121159 A1 | 4/2025 | Howell et al. | |
| 2025/0121165 A1 | 4/2025 | Howell | |

FOREIGN PATENT DOCUMENTS

| | | | | |
|---|---|---|---|---|
| CN | 116322869 A | 6/2023 | | |
| EP | 0641571 A1 | 3/1995 | | |
| EP | 0730880 A1 | 9/1996 | | |
| EP | 2061385 A1 | 5/2009 | | |
| EP | 1458437 B1 | 3/2010 | | |
| EP | 2248549 A2 | 11/2010 | | |
| EP | 2319576 A1 | 5/2011 | | |
| EP | 2366422 A1 | 9/2011 | | |
| EP | 2433670 A1 | 3/2012 | | |
| EP | 2486880 A2 | 8/2012 | | |
| EP | 2486881 A2 | 8/2012 | | |
| EP | 2486951 A2 | 8/2012 | | |
| EP | 2512576 A2 | 10/2012 | | |
| EP | 2152348 B1 | 2/2015 | | |
| EP | 3205368 A1 | 8/2017 | | |
| EP | 3093038 B1 | 5/2019 | | |
| EP | 2260897 B1 | 9/2019 | | |
| EP | 3725356 A1 | * | 10/2020 | A61M 25/0606 |
| EP | 3730179 A1 | 10/2020 | | |
| GB | 1273547 A | 5/1972 | | |
| NO | 2019199734 A1 | 10/2019 | | |
| WO | 9306878 A1 | 4/1993 | | |
| WO | 94/21315 A1 | 9/1994 | | |
| WO | 95/32009 A2 | 11/1995 | | |
| WO | 98/44979 A1 | 10/1998 | | |
| WO | 98/53871 A1 | 12/1998 | | |
| WO | 99/12600 A1 | 3/1999 | | |
| WO | 99/26681 A1 | 6/1999 | | |
| WO | 02/05886 A1 | 1/2002 | | |
| WO | 2003008020 A1 | 1/2003 | | |
| WO | 2003057272 A2 | 7/2003 | | |
| WO | 2003066125 A2 | 8/2003 | | |
| WO | 2006055288 A2 | 5/2006 | | |
| WO | 2006055780 A2 | 5/2006 | | |
| WO | 2006/096262 A2 | 9/2006 | | |
| WO | 2007046850 A2 | 4/2007 | | |
| WO | 2008005618 A2 | 1/2008 | | |
| WO | 2008033983 A1 | 3/2008 | | |
| WO | 2008092029 A2 | 7/2008 | | |
| WO | 2008/107869 A1 | 9/2008 | | |
| WO | 2008/131300 A2 | 10/2008 | | |
| WO | 2008131289 A2 | 10/2008 | | |
| WO | 2008133808 A1 | 11/2008 | | |
| WO | 2009114833 A1 | 9/2009 | | |
| WO | 2009114837 A2 | 9/2009 | | |
| WO | 2010/048449 A2 | 4/2010 | | |
| WO | 2010056906 A2 | 5/2010 | | |
| WO | 2010083467 A2 | 7/2010 | | |
| WO | 2010/132608 A2 | 11/2010 | | |
| WO | 2011081859 A2 | 7/2011 | | |
| WO | 2011097639 A2 | 8/2011 | | |
| WO | 2011146764 A1 | 11/2011 | | |
| WO | 2012068162 A2 | 5/2012 | | |
| WO | 2012068166 A2 | 5/2012 | | |
| WO | 2012135761 A1 | 10/2012 | | |
| WO | 2012162677 A1 | 11/2012 | | |
| WO | 2013026045 A1 | 2/2013 | | |
| WO | 2013138519 A1 | 9/2013 | | |
| WO | 2014006403 A1 | 1/2014 | | |
| WO | 2014/100392 A1 | 6/2014 | | |
| WO | 2014113257 A2 | 7/2014 | | |
| WO | 2014152005 A2 | 9/2014 | | |
| WO | 2014197614 A2 | 12/2014 | | |
| WO | 2015057766 A1 | 4/2015 | | |
| WO | 2016110824 A1 | 7/2016 | | |
| WO | 2016123278 A1 | 8/2016 | | |
| WO | 2016139590 A1 | 9/2016 | | |
| WO | 2016139597 A2 | 9/2016 | | |
| WO | 2016176065 A1 | 11/2016 | | |
| WO | 2018089275 A1 | 5/2018 | | |
| WO | 2018089285 A1 | 5/2018 | | |
| WO | 2018089385 A1 | 5/2018 | | |
| WO | 2018191547 A1 | 10/2018 | | |
| WO | 2018213148 A1 | 11/2018 | | |
| WO | 2018218236 A1 | 11/2018 | | |
| WO | 2019/146026 A1 | 8/2019 | | |
| WO | 2020069395 A1 | 4/2020 | | |
| WO | 2021050302 A1 | 3/2021 | | |
| WO | 2021/077103 A1 | 4/2021 | | |
| WO | 2021062023 A1 | 4/2021 | | |
| WO | 2021081205 A1 | 4/2021 | | |
| WO | 2021086793 A1 | 5/2021 | | |
| WO | 2022/120068 A1 | 6/2022 | | |
| WO | 2022/133138 A2 | 6/2022 | | |
| WO | 2023069600 A1 | 4/2023 | | |
| WO | 2023069726 A1 | 4/2023 | | |
| WO | 2023167940 A1 | 9/2023 | | |
| WO | 2024238400 A1 | 11/2024 | | |

OTHER PUBLICATIONS

PCT/US2022/047444 filed Oct. 21, 2022 International Search Report and Written Opinion dated Mar. 7, 2023.

U.S. Appl. No. 17/079,320, filed Oct. 23, 2020 Restriction Requirement dated Mar. 29, 2023.

U.S. Appl. No. 17/079,320, filed Oct. 23, 2020 Non-Final Office Action dated May 7, 2024.

U.S. Appl. No. 17/079,320, filed Oct. 23, 2020 Notice of Allowance dated Aug. 20, 2024.

U.S. Appl. No. 17/200,630, filed Mar. 12, 2021 Advisory Action dated May 10, 2024.

U.S. Appl. No. 17/200,630, filed Mar. 12, 2021 Non-Final Office Action dated Jun. 4, 2024.

U.S. Appl. No. 17/200,630, filed Mar. 12, 2021 Notice of Allowance dated Sep. 11, 2024.

U.S. Appl. No. 17/553,609, filed Dec. 16, 2021 Non-Final Office Action dated Oct. 15, 2024.

U.S. Appl. No. 17/540,988, filed Dec. 2, 2021 Final Office Action dated May 16, 2025.

U.S. Appl. No. 17/540,988, filed Dec. 2, 2021 Notice of Allowance dated Aug. 1, 2025.

U.S. Appl. No. 17/553,609, filed Dec. 16, 2021 Non-Final Office Action dated Oct. 9, 2025.

U.S. Appl. No. 17/971,182, filed Oct. 21, 2022 Restriction Requirement dated Aug. 26, 2025.

Strittmatter, F., Eisel, M., Brinkmann, R., Cordes, J., Lange, B., & Sroka, R., "Laser Induced Lithotripsy: a Review, insight into laboratory work, and lessons learned." Translational Biophotonics, 2(1-2), e201900029. (2020).

(56)     References Cited

OTHER PUBLICATIONS

Traxer, O., & Keller, E. X., "Thulium fiber laser: the new player for kidney stone treatment? A comparison with Holmium: YAG laser." World Journal of Urology, 38, 1883-1894. (2020).

U.S. Appl. No. 17/079,320, filed Oct. 23, 2020 Advisory Action dated Apr. 11, 2024.

U.S. Appl. No. 17/079,320, filed Oct. 23, 2020 Final Office Action dated Jan. 18, 2024.

U.S. Appl. No. 17/200,566, filed Mar. 12, 2021 Final Office Action dated Dec. 28, 2023.

U.S. Appl. No. 17/200,566, filed Mar. 12, 2021 Notice of Allowance dated Apr. 3, 2024.

U.S. Appl. No. 17/200,630, filed Mar. 12, 2021 Final Office Action dated Feb. 5, 2024.

PCT/US2020/057202 filed Oct. 23, 2020 International Preliminary Report on Patentability dated Apr. 26, 2022.

PCT/US2020/057202 filed Oct. 23, 2020 International Search Report and Written Opinion dated Jan. 21, 2021.

PCT/US2021/022208 filed Mar. 12, 2021 International Search Report and Written Opinion dated Sep. 3, 2021.

PCT/US2021/022226 filed Mar. 12, 2021 International Search Report and Written Opinion dated Oct. 21, 2021.

PCT/US2021/061638 filed Dec. 2, 2021 International Search Report and Written Opinion dated Apr. 12, 2022.

PCT/US2021/063903 filed Dec. 16, 2021, International Search Report and Written Opinion dated Jun. 28, 2022.

U.S. Appl. No. 17/540,988, filed Dec. 2, 2021 Non-Final Office Action dated Jan. 22, 2025.

U.S. Appl. No. 17/553,609, filed Dec. 16, 2021 Advisory Action dated Apr. 29, 2025.

U.S. Appl. No. 17/553,609, filed Dec. 16, 2021 Final Office Action dated Jan. 31, 2025.

PCT/US2023/014295 filed Mar. 1, 2023 International Search Report and Written Opinion dated Jun. 23, 2023.

U.S. Appl. No. 17/079,320, filed Oct. 23, 2020 Non-Final Office Action dated Jul. 28, 2023.

U.S. Appl. No. 17/200,566, filed Mar. 12, 2021 Restriction Requirement dated Jul. 14, 2023.

U.S. Appl. No. 17/200,566, filed Mar. 12, 2021 Non-Final Office Action dated Oct. 6, 2023.

U.S. Appl. No. 17/200,630, filed Mar. 12, 2021 Non-Final Office Action dated Sep. 27, 2023.

U.S. Appl. No. 17/200,630, filed Mar. 12, 2021 Restriction Requirement dated Jul. 14, 2023.

U.S. Appl. No. 17/971,182, filed Oct. 21, 2022 Non-Final Office Action dated Jan. 28, 2026.

U.S. Appl. No. 18/116,232, filed Mar. 1, 2023 Non-Final Office Action dated Feb. 5, 2026.

U.S. Appl. No. 18/116,232, filed Mar. 1, 2023 Restriction Requirement dated Nov. 14, 2025.

PCT/US2025/052712 filed Oct. 27, 2025 International Search Report and Written Opinion dated Feb. 19, 2026.

* cited by examiner

Proximal                                                 Distal

Proximal

Distal

Proximal                                      Distal

GUIDEWIRE STABILIZATION SYSTEM FOR RAPIDLY INSERTED CENTRAL CATHETER (RICC) PLACEMENT SYSTEM

PRIORITY

This application claims the benefit of priority to U.S. Provisional Application No. 63/270,489, filed Oct. 21, 2021, which is incorporated by reference in its entirety into this application.

SUMMARY

Briefly summarized, embodiments disclosed herein are directed to a guidewire stabilization system for a Rapidly Inserted Central Catheter (RICC) placement system, and associated methods thereof. When placing a catheter, e.g. a RICC catheter, it can be advantageous to obtain and stabilize venous access as soon as possible after venipuncture. To achieve this, a distal tip of a guidewire can reside within a needle lumen during venipuncture. Once venous access has been confirmed, the guidewire can be advanced into the vasculature to maintain patency of the access site. The needle can then be removed, preferably in such a way so as to leave the guidewire in place.

Some RICC placement systems utilize a slotted needle including a sheath disposed thereover. A distal tip of the guidewire can remain in position within the vasculature and a portion of the guidewire can pass through the needle slot as the needle is withdrawn proximally. A sheath can cover the slot and maintain the integrity of the needle lumen, e.g. to prevent fluid leakage through the slot. As the guidewire passes through the needle slot the guidewire can tear the sheath. However, as the guidewire passes through the needle slot, forces acting on the guidewire can dislodge the position of the guidewire distal tip within the vasculature. Embodiments disclosed herein are directed to a guidewire stabilization system configured to couple with a RICC catheter placement system and stabilize the guidewire in position as the needle is withdrawn proximally from the access site.

Disclosed herein is a catheter placement system including, a needle extending along a longitudinal axis and supported by a needle hub, the needle defining a needle lumen and including an aperture extending through a wall of the needle adjacent the hub, and a slot extending from the aperture to a distal tip of the needle, a guidewire having a distal tip extending through the aperture and into the needle lumen, and a guidewire stabilization system including, a housing coupled to the needle hub and defining a needle channel having a portion of the needle disposed therethrough, and a stabilization mechanism transitionable between a locked position and an unlocked position, the stabilization mechanism configured to grip a portion of the guidewire in the locked position to stabilize the guidewire relative to the housing as the needle is withdrawn proximally from the needle channel of the housing.

In some embodiments, the stabilization mechanism is biased towards the unlocked position and includes an actuator button configured to be actuated and transition the stabilization mechanism from the unlocked position to the locked position. In some embodiments, the actuator button is further configured to disengage the needle hub from the housing. In some embodiments, the stabilization mechanism further includes a first lever and a second lever each pivotably coupled to the housing, the first lever defining a first actuator button and the second lever defining a second actuator button. In some embodiments, a first gripping surface of the first lever and a second gripping surface of the second lever contact the guidewire in the locked position and inhibit axial movement thereof.

In some embodiments, one or both of the first gripping surface and the second gripping surface are in a spaced apart relationship from the guidewire in the unlocked position. In some embodiments, one or both of the first gripping surface and the second gripping surface engage the guidewire in the unlocked position to allow the guidewire to slide axially from a first position to a second position and to maintain the guidewire in the second position until repositioned. In some embodiments, one or both of the first lever and the second lever include a first material, and the gripping surface includes a second material, different from the first material and including a high frictional co-efficient relative to the first material.

In some embodiments, the second material includes one of a plastic, polymer, elastomer, rubber, or silicone rubber. In some embodiments, the first gripping surface includes one of a first protrusion or a first detent configured to engage one of a second protrusion or a second detent disposed on the second gripping surface. In some embodiments, the stabilization mechanism includes a first lever, hingedly coupled to the housing and defining a gripping surface configured to extend into a guidewire channel of the housing and impinge on the guidewire in the locked position. In some embodiments, the gripping surface is configured to deflect a portion of the guidewire from a linear configuration to a non-linear configuration in the locked position to inhibit axial movement of the guidewire.

In some embodiments, the gripping surface is configured to compress a portion of the guidewire against a wall of the guidewire channel to inhibit axial movement of the guidewire in the locked position. In some embodiments, the stabilization mechanism includes a clamp having a gripping surface and slidably engaged with the housing between the locked position and the unlocked position along a first axis extending perpendicular to a second axis of the guidewire, the gripping surface angled relative to the first axis. In some embodiments, the gripping surface engages a portion of the guidewire in the locked position and compresses the portion of the guidewire against a wall of a guidewire channel along a third axis extending at an angle to both the first axis and the second axis.

In some embodiments, the stabilization system includes a cam rotatable between the locked position and the unlocked position, the cam including a first notch that aligns with the guidewire channel in the unlocked position and a second notch that aligns with the guidewire channel in the locked position, the second notch configured to compress a portion of the guidewire against a wall of a guidewire channel to inhibit axial movement of the guidewire in the locked position. In some embodiments, the cam is bistable in both the locked position and the unlocked position. In some embodiments, the cam further includes a lever extending therefrom and configured to indicate to a user that the cam is in one of the locked or unlocked positions.

In some embodiments, the stabilization system further includes an inner housing, slidably engaged with a housing channel of the housing and configured to be urged proximally as the needle is withdrawn, and deflect an arm of the inner housing from the unlocked position to the locked position to inhibit axial movement of the guidewire. In some embodiments, the inner housing defines a portion of the needle channel and is configured to slidably engage the needle in an interference fit engagement to urge the inner housing proximally as the needle is withdrawn from the needle channel. In some embodiments, the inner housing further includes a tapered proximal end configured to engage a tapered proximal end of the housing channel and deflect the arm to the locked position as the needle is withdrawn from the needle channel.

In some embodiments, the inner housing includes a first arm defining a first gripping surface and a second arm defining a second gripping surface disposed opposite the first gripping surface across an axis of the guidewire, the first arm and the second arm configured to deflect inwards to grip a portion of the guidewire therebetween in the locked position. In some embodiments, the stabilization mechanism is biased towards the locked position and includes an actuator button configured to transition a gripping surface of the stabilization mechanism from the locked position to the unlocked position.

In some embodiments, the catheter placement system further includes a clamp arm slidably engaged with the housing between a locked position and an unlocked position, a first surface of the clamp arm defining the actuator button and a second surface of the clamp arm defining the gripping surface and configured to compress a portion of the guidewire against a wall of a guidewire channel to inhibit axial movement of the guidewire in the locked position. In some embodiments, the catheter placement system further includes a compression spring configured to bias the clamp arm to the locked position.

Also disclosed is a method of stabilizing a guidewire during placement of a catheter including, accessing a vasculature with a needle supported by a needle hub and defining a needle lumen, the needle including an aperture extending through a wall of the needle adjacent the hub, and a slot extending from the aperture to a distal tip of the needle, advancing a distal tip of a guidewire through the needle lumen and into the vasculature, transitioning a guidewire stabilization system to a locked position to inhibit axial movement of the guidewire relative to a housing of the guidewire stabilization system, and withdrawing the needle proximally from vasculature.

In some embodiments, the method further includes actuating an actuator button to transition the guidewire stabilization system from a locked position to an unlocked position, the guidewire stabilization system biased towards the unlocked position. In some embodiments, the method further includes actuating the actuator button to disengage the needle hub from the housing. In some embodiments, the method further includes applying opposing forces to the guidewire stabilization system, perpendicular to an axis of the guidewire to transition a first lever and a second lever of the guidewire stabilization system to the locked position.

In some embodiments, the method further includes engaging a first gripping surface of the first lever and a second gripping surface of the second lever with the guidewire in the locked position to inhibit axial movement thereof. In some embodiments, one or both of the first gripping surface and the second gripping surface engage the guidewire in the unlocked position to allow the guidewire to slide axially from a first position to a second position and to maintain the guidewire in the second position until repositioned. In some embodiments, the method further includes impinging a gripping surface of the guidewire stabilization system on the guidewire and deflecting a portion of the guidewire from a linear configuration in the unlocked position, to a non-linear configuration in the locked position.

In some embodiments, the method further includes impinging a gripping surface of the guidewire stabilization system on the guidewire and compressing a portion of the guidewire against a wall of a guidewire channel of the housing, in the locked position. In some embodiments, the method further includes sliding a clamp, having a gripping surface, along a first axis extending perpendicular to a second axis of the guidewire and deflecting a portion of the guidewire along a third axis, extending at an angle to both the first axis and the second axis, and gripping the portion of the guidewire against a wall of a guidewire channel in the locked position, the gripping surface angled relative to the first axis and the third axis.

In some embodiments, the method further includes rotating a cam, including a lever extending therefrom, between the unlocked position and the locked position about an axis extending parallel to an axis of the guidewire, the cam bi-stable in the unlocked position and the locked position. In some embodiments, the method further includes sliding an inner housing proximally relative to the housing and deflecting an arm of the inner housing to impinge a gripping surface with the guidewire to inhibit axial movement of the guidewire. In some embodiments, the method further includes engaging a tapered proximal end of the inner housing with a tapered proximal end of a housing channel of the housing to deflect the arm inwards to the locked position and inhibiting axial movement of the guidewire.

In some embodiments, transitioning a guidewire stabilization system to a locked position includes biasing a clamp arm using a biasing member to the locked position, and wherein transitioning the guidewire stabilization system to an unlocked position includes applying a force to the clamp arm to overcome the force of the biasing member and slide the clamp arm to disengage the guidewire.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
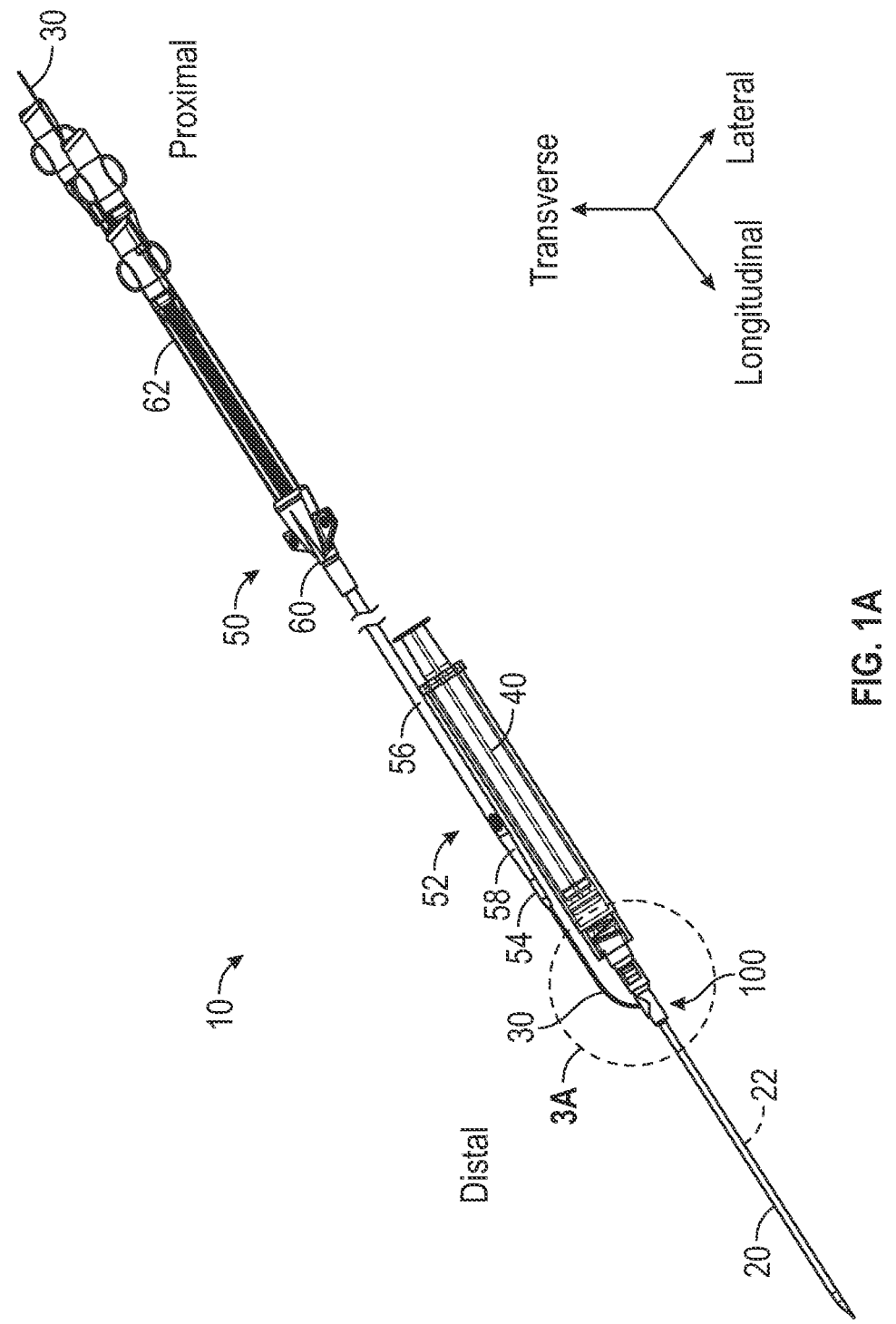
FIG. 1A shows a perspective view of an exemplary RICC placement system in an unfolded state, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle, however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle, however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

Figure 1B:
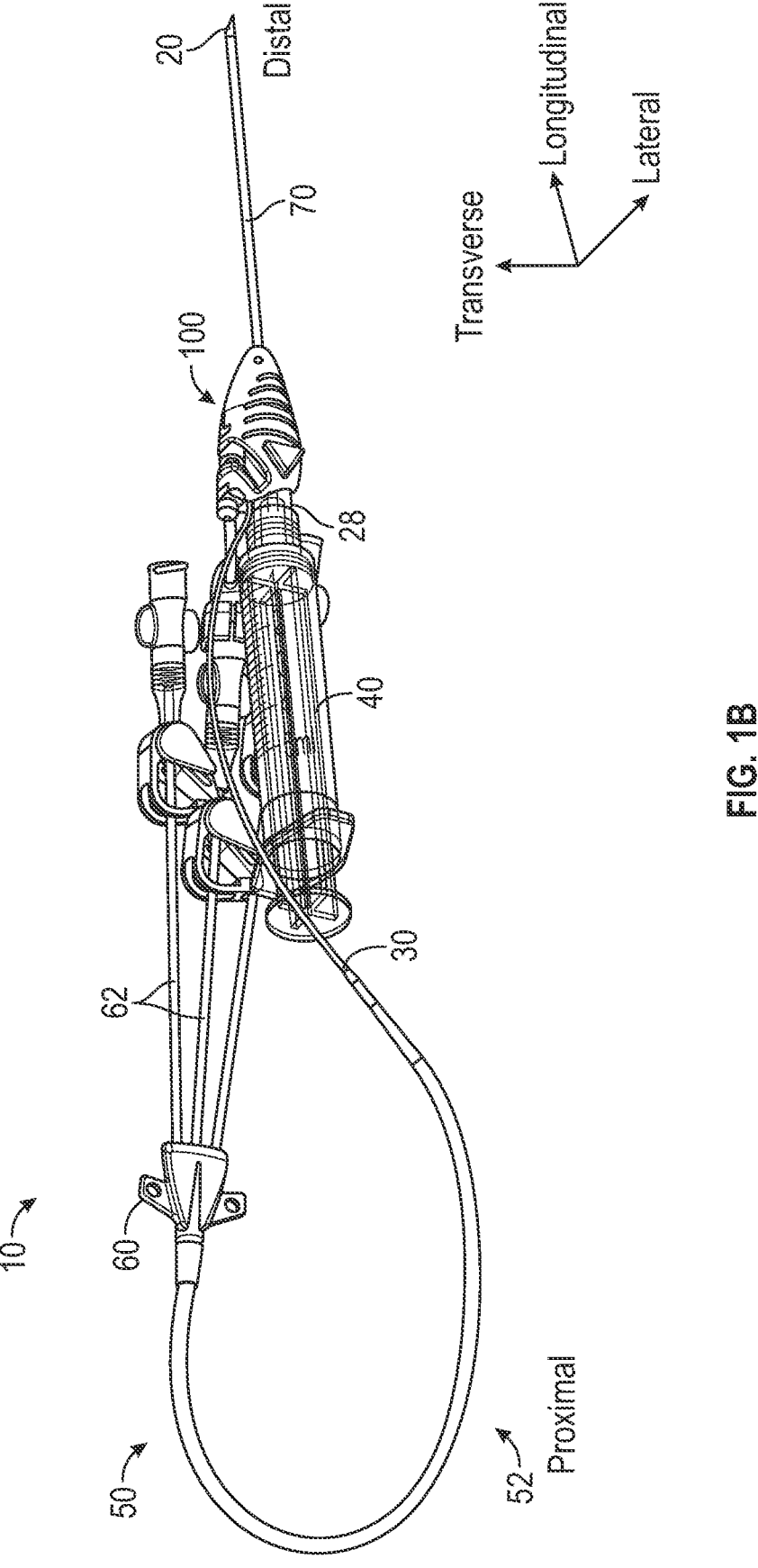
FIG. 1B shows a perspective view of an exemplary RICC placement system in a folded state ready for use, in accordance with embodiments disclosed herein.
Figure 1C:
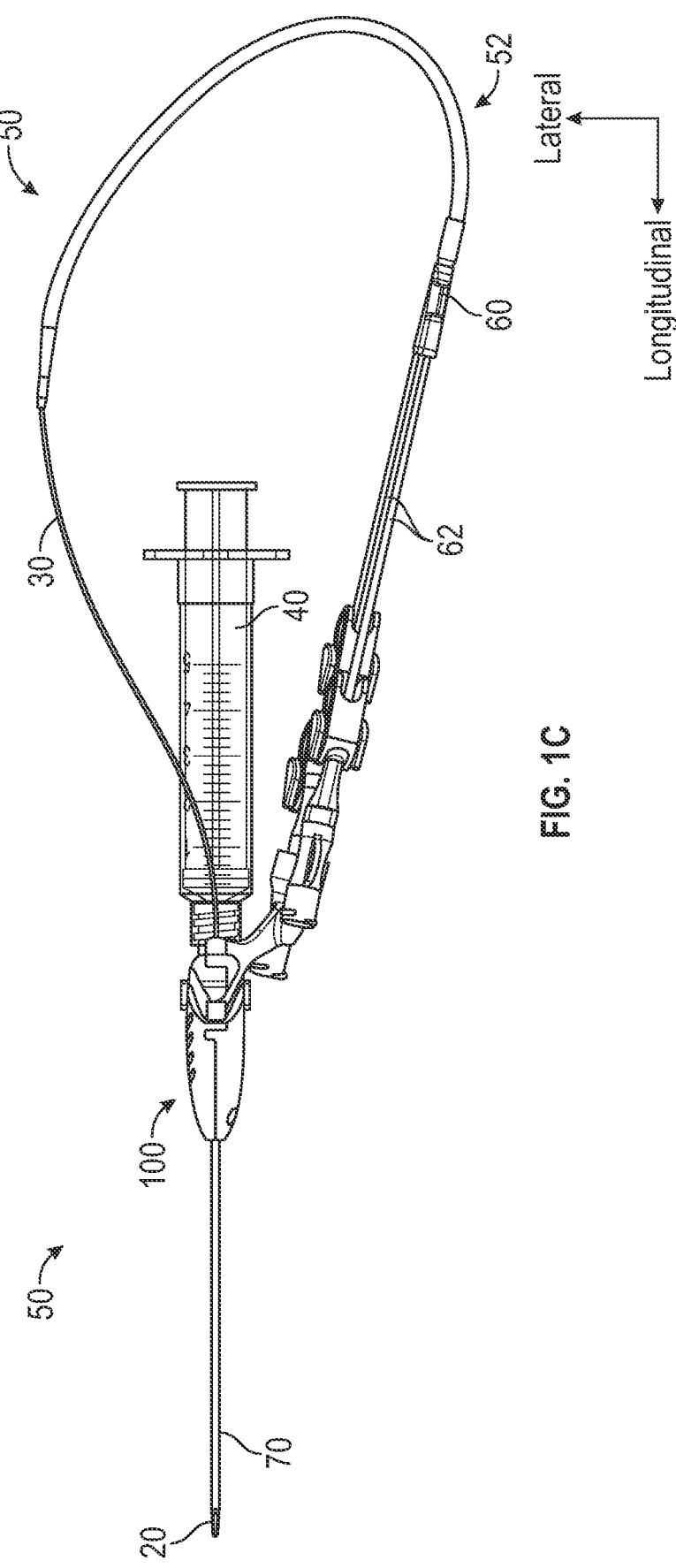
FIG. 1C shows a plan view of an exemplary RICC placement system in a folded state ready for use, in accordance with embodiments disclosed herein.

To assist in the description of embodiments described herein, as shown in FIGS. 1A-1C, a longitudinal axis extends substantially parallel to an axis of the needle 20. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

FIGS. 1A-1C show details of an exemplary Rapidly Insertable Central Catheter (RICC) placement system ("placement system") 10 generally including a needle 20, a guidewire 30, a syringe system 40, and a RICC catheter 50. The RICC catheter 50 can generally include a catheter 52 supported at a proximal end by a catheter hub ("hub") 60. The hub 60 can include one or more extension legs 62 extending proximally therefrom. Each extension leg 62 of the one or more extension legs can be in fluid communication with a lumen of the catheter 52. The catheter 52 can include a first section 54 disposed distally and defining a single lumen, a second section 56 disposed proximally and defining two or more lumen, and a dilator section 58 disposed therebetween. A guidewire 30 can extend through a lumen of the RICC catheter 50 from a proximal end of an extension leg 62, to a distal tip of the first section 54.

In an exemplary method of placing the RICC catheter 50, the needle 20 can be urged distally into the patient and access a vasculature, forming an insertion site. A syringe system 40, or similar device can draw a fluid flow proximally through a needle lumen 22 to observe a color and/or pulsatile flow and confirm correct vascular access. Once correct vascular access has been confirmed, the guidewire 30 can then be advanced through the needle lumen 22 and into the vasculature to maintain patency of the insertion site. The needle 20 and syringe system 40 assembly can then be withdrawn proximally. In an embodiment, a distal tip of the guidewire 30 can reside within the needle lumen 22 during venipuncture, which can expedite accessing the vasculature once venous access is confirmed and maintain patency of the insertion site. In an embodiment, the needle 20 can include a slot 26 configured to facilitate removal of the needle 20 and syringe system 40 from the guidewire 30 while leaving the guidewire 30 in place, as described in more detail herein.

The RICC 50 can then be advanced over the guidewire 30 and into the vasculature. The first section 54 of the RICC 50, having only a single lumen and defining a relatively smaller outer diameter, can enter the vasculature over the guidewire 30. The dilator section 58 can then dilate the insertion site to allow the relatively larger diameter second section 56, defining two or more lumen, to enter the vasculature. Once the RICC 50 has been placed, the guidewire 30 can be withdrawn proximally. Further details and embodiments of RICC systems 10 can be found, for example, in U.S. Pat. No. 10,376,675, U.S. 2019/0255294, U.S. 2021/0069471, U.S. 2021/0085927, U.S. 2021/0113809, U.S. 2021/0113810, U.S. 2021/0121661, U.S. 2021/0228843, U.S. 2021/0283368, U.S. 2021/0283381, U.S. 2021/0322729, U.S. 2021/0330941, U.S. 2021/0330942, U.S. 2021/0361915, U.S. 2021/0379336, U.S. 2021/0402142, U.S. 2021/0402149, U.S. 2021/0402153, U.S. 2021/0121667, U.S. 2022/0001138, U.S. 2022/0032013, U.S. 2022/0032014, U.S. 2022/0062528, U.S. 2022/0126064, U.S. 2022/0152368, U.S. 2022/0176081, U.S. 2022/0176082, U.S. 2022/0193376, U.S. 2022/0193377, U.S. 2022/0193378, U.S. 2022/0193379, and U.S. 2022/0296862, each of which is incorporated by reference in its entirety into this application.

Figures 2A, 2B:
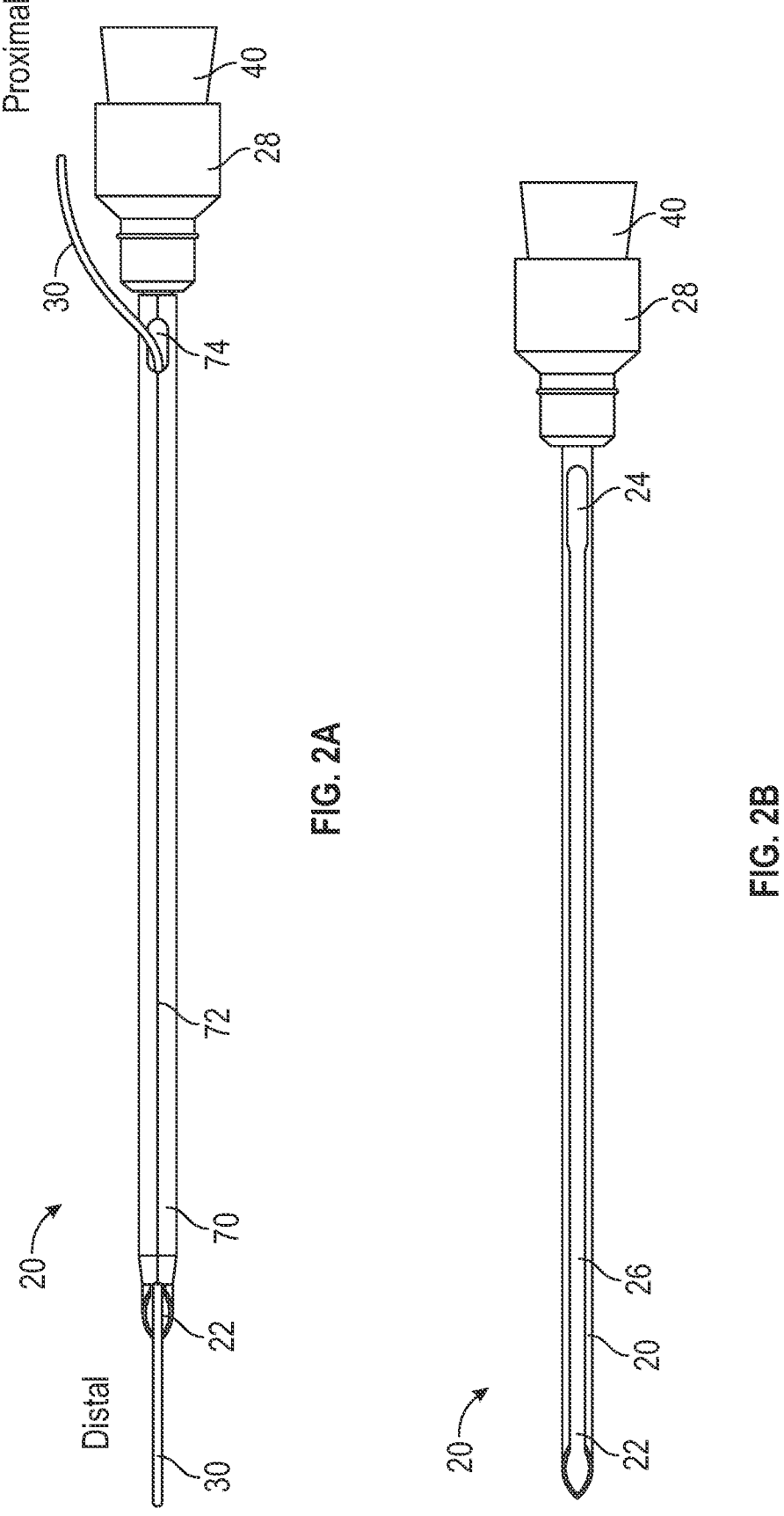
FIG. 2A shows a plan view of a needle, sheath and guidewire assembly of the RICC placement system of FIG. 1A, in accordance with embodiments disclosed herein.
FIG. 2B shows a plan view of a slotted needle of the RICC placement system of FIG. 1A, in accordance with embodiments disclosed herein.

FIGS. 2A-2B show further details of the slotted needle 20 of the RICC system 10. The needle 20 can define a lumen 22 and can be supported at a proximal end by a needle hub 28. The needle hub 28 can be coupled to the syringe system 40 and can provide fluid communication between the syringe system 40 and the needle lumen 22. In an embodiment, the needle 20 can include a guidewire aperture 24 disposed in a side wall of the needle 20, adjacent the needle hub 28 and communicating with the needle lumen 22. The guidewire aperture 24 can be configured to receive a portion of the guidewire 30 extending therethrough and into to the needle lumen 22. In an embodiment, a distal tip of the guidewire 30 can be disposed within the needle lumen 22 as the needle 20 accesses the vasculature. Once the needle 20 has accessed the vasculature, the distal tip of the guidewire 30 can extend distally of a distal tip of the needle 20. Advantageously, this allows for rapid stabilization of the insertion site soon after venipuncture, securing the insertion site and expediting the placement process.

In an embodiment, the needle 20 can further include a needle slot 26 extending longitudinally between the guidewire aperture 24 and a distal tip of the needle 20. In an embodiment, a lateral width of the needle slot 26 can be equal to or greater than a diameter of the guidewire 30. As such, a portion of the guidewire 30 can pass through the needle slot 26 to allow the needle 20 to disengage the guidewire 30. In an embodiment, a lateral width of the needle slot 26 can be equal to or less than a diameter of the guidewire 30. In an embodiment, a first edge of the needle slot 26 can contact a second edge of the needle slot 26, opposite the first edge across a central longitudinal axis of the needle 20 to define a slit. In an embodiment, the first edge and the second edge of the needle slot 26 can be configured to flex laterally, or radially, outward and allow a portion of the guidewire 30 to pass through the needle slot 26 to allow the needle 20 to disengage the guidewire 30.

In an embodiment, the needle 20 can further include a sheath 70 disposed on an outer surface the needle 20. In an embodiment, the sheath 70 can be formed of a plastic, polymer, or similar suitable material. The sheath 70 can fit tightly about the needle 20, over the slot 26 and prevent any fluid from passing through the slot 26 to maintain the integrity of the needle lumen 22. In an embodiment, the sheath 70 can include a sheath guidewire aperture 74 disposed in a side wall of the sheath 70, adjacent a proximal end of the sheath 70 and aligned with the needle guidewire aperture 24 to communicate with the needle lumen 22. The sheath guidewire aperture 74 can be configured to receive a portion of the guidewire 30 extending therethrough and into to the needle lumen 22.

In an embodiment, the sheath 70 can include a tear line 72, extending longitudinally between the sheath guidewire aperture 74 and a distal end of the sheath 70. The tear line 72 can include a groove, score line, perforation, laser cut line, or similar line of weakness configured to allow the sheath 70 to separate therealong as the guidewire 30 is urged through the needle slot 26. In an embodiment, the placement system 10 can further include a blade configured to cut the sheath 70 along the tear line 72 to facilitate disengaging the guidewire 30 from the needle 20. In an embodiment, the placement system 10 can include a dowel pin, or similar support structure, disposed proximally of the guidewire 30 and adjacent the tear line 72 to support a portion of the guidewire 30 as the sheath 70 is urged thereover.

In an exemplary method of use, the needle 20 and sheath 70 assembly can be urged distally to form an insertion site, as described herein. A fluid flow can flow proximally through the needle 22. The sheath 70 disposed over the slot 26 can prevent fluid from leaking from the lumen 22, through the slot 26. In an embodiment, a vacuum can be applied to the needle lumen 22, for example by the syringe system 40, to draw a fluid flow therethrough. Advantageously, the sheath 70 can maintain integrity of the needle lumen 22 to prevent fluid being drawn through the slot 26, and instead draw a fluid through a distal opening of the needle lumen, adjacent the distal tip. To note, a valve or gasket can be aligned with the sheath guidewire aperture 74 and the needle guidewire aperture 24 to prevent any fluid leakage therethrough.

Once vascular access has been confirmed, the needle 20 can be withdrawn proximally. To allow the guidewire 30 to remain in position as the needle 20 is withdrawn proximally, a portion of the guidewire 30 can pass through the slot 26 from the guidewire aperture 24 to a distal end of the needle 20. As the guidewire 30 passes through the slot 26, the guidewire 30 can tear the sheath 70 along the tear line 72 allowing the guidewire 30 to separate from the needle 20 and sheath 70 assembly. As will be appreciated, various apparatus and methods of removing the needle 20 while leaving the guidewire 30 in place within the vasculature are contemplated to fall within the scope of the present invention. Further details and embodiments of such systems can be found in U.S. patent application Ser. No. 17/746,113 filed May 17, 2022, and U.S. patent application Ser. No. 17/883, 490 filed Aug. 8, 2022, each of which is incorporated by reference in its entirety into this application.

In an embodiment, the RICC placement system 10 can include a guidewire stabilization system 100 configured to stabilize the guidewire 30 relative to the insertion site, as the needle 20 is withdrawn proximally. Advantageously, the guidewire stabilization system 100 can mitigate any movement of the guidewire 30 within the vasculature, or prevent inadvertent removal of the guidewire 30 from the vasculature.

Figure 3A:
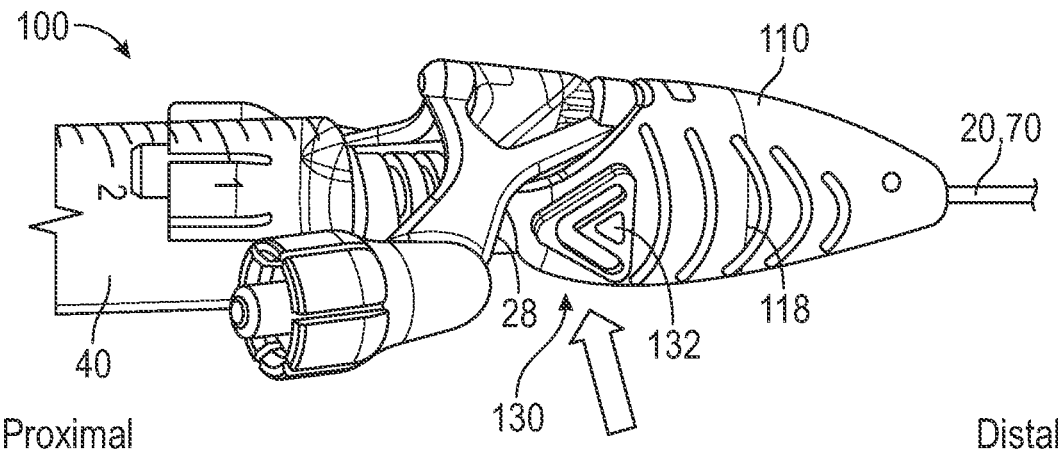
FIGS. 3A-3B show perspective views of a guidewire stabilization system, in accordance with embodiments disclosed herein.
Figure 3B:
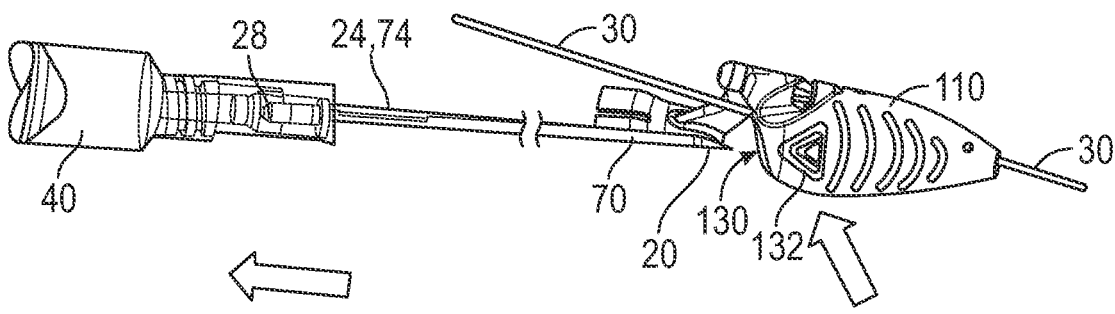

In an embodiment, as shown in FIGS. 3A-3B, the guidewire stabilization system 100 can generally include a housing 110 and a stabilization mechanism 130. The stabilization mechanism 130 can include one or more actuator buttons ("button") 132. In an embodiment, actuating the button 132 can cause the stabilization mechanism 130 to transition to a locked position to grip the guidewire 30 and prevent movement of the guidewire 30 relative to the housing 110. In an embodiment, actuating the button 132 can further actuate releasing the needle hub 28 from housing 110. In an embodiment, releasing the button 132 can transition the stabilization mechanism 130 to an unlocked position to allow the guidewire 30 to slide relative to the housing 110. In an embodiment, releasing the button 132 can actuate disengaging the housing 110 from the guidewire 30. In an embodiment, a first actuation of the button 132 can cause the stabilization mechanism 130 to transition from the unlocked position to the locked position and remain in the locked position after the button 132 has been released by the user. In an embodiment, a second actuation of the button 132 can cause the stabilization mechanism 130 to transition from the locked position to the unlocked position. Advantageously, this allows the clinician to continue to grip the guidewire 30 and prevent axial movement without having to maintain pressure on the actuator button 132. In an embodiment, a first actuation of the button 132 can also release the needle hub 28, and a second actuation of the button 132 can also release the guidewire 30 from the housing 110. These and other combinations of actions and actuations are also contemplated to fall within the scope of the present invention.

In an embodiment, one or both of the housing 110 or button 132 can include a gripping feature 118 configured to facilitate grasping the housing 110 while the syringe system 40 and/or needle 20 and sheath 70 assembly are withdrawn proximally, as shown in FIG. 3B. The gripping feature 118 can include one or more ridges, ribs, wings, handles, detents, recesses or similar structures disposed on a surface thereof to facilitate grasping the housing 110. In an embodiment, the gripping feature 118 can include a second material, different from a first material of the housing 110, and providing an increased friction co-efficient. Exemplary second materials can include plastic, polymer, elastomer, rubber, silicone rubber, or the like.

In use, as shown in FIG. 3B, a clinician can grasp the housing 110 and actuate the button 132 with a first hand to grip the guidewire 30, and stabilize the housing 110 and guidewire 30 assembly relative to the insertion site. The clinician can then grasp the syringe system 40 and/or needle hub 28 with a second hand and disengage the needle hub 28 from the housing 110 and withdraw the needle 20 proximally to disengage the needle 20 from guidewire 30. Advantageously, the housing 110 and stabilization mechanism 130 can mitigate movement of the guidewire 30 relative to the vasculature. Further, the stabilization system 130 can allow a clinician to stabilize the housing 110, actuate the actuator button 132 and/or disengage the needle hub 28 from the housing 110, or combinations thereof, with a single hand or in a single action. In an embodiment, the stabilization mechanism 130 can include one or more levers, cams, protrusions and detents, biasing members, gears, arms, wedges, or the like, as described in more detail herein, and can provide mechanical advantage to gripping the guidewire 30. As such, less force is required from the clinician to actuate the stabilization mechanism 130 and apply a gripping force to the guidewire 30. This can be important where the guidewire 30 further includes lubricious coatings, or the like.

FIGS. 4A-4E show details of an embodiment of a guidewire stabilization system 100 including a pinch-activated guidewire stabilization system 430. In an embodiment, the housing 110 can define a needle channel 112 and a guidewire channel 114, communicating with the needle channel 112 and extending at an angle therefrom. The needle channel 112 can be configured to receive a portion of the needle 20 therethrough. When the needle 20 is engaged with the housing 110, the guidewire aperture 24 of the needle 20 can align with the guidewire channel 114. As such, the guidewire 30 can extend through the guidewire channel 114, through the guidewire aperture 24 of the needle 20 and into the needle lumen 22. In an embodiment, a proximal end of the housing 110 can releasably engage the needle hub 28 in an interference fit, press fit, snap fit, or locking fit engagement. In an embodiment, actuating the guidewire stabilization system 430 to grip the guidewire 30 can further include disengaging, or unlocking, the needle hub 28 from the housing 110. In an embodiment, a proximal end of the needle hub 28 can releasably engage a syringe system 40 in a press-fit, snap-fit, snap-fit, luer lock, threaded engagement, combinations thereof, or the like.

In an embodiment, the pinch-activated stabilization system 430 can include one or more levers 432 hingedly coupled with the housing and pivotable between a locked position and an unlocked position. In an embodiment, the pinch-activated stabilization system 430 can include a biasing member configured to bias the stabilization system 430 to the unlocked position. In an embodiment, a surface of the lever 432, e.g. a first surface, can define an actuator button 132. In an embodiment, a surface of the lever 432, e.g. a second surface, can include a gripping feature 118.

Figure 4A:
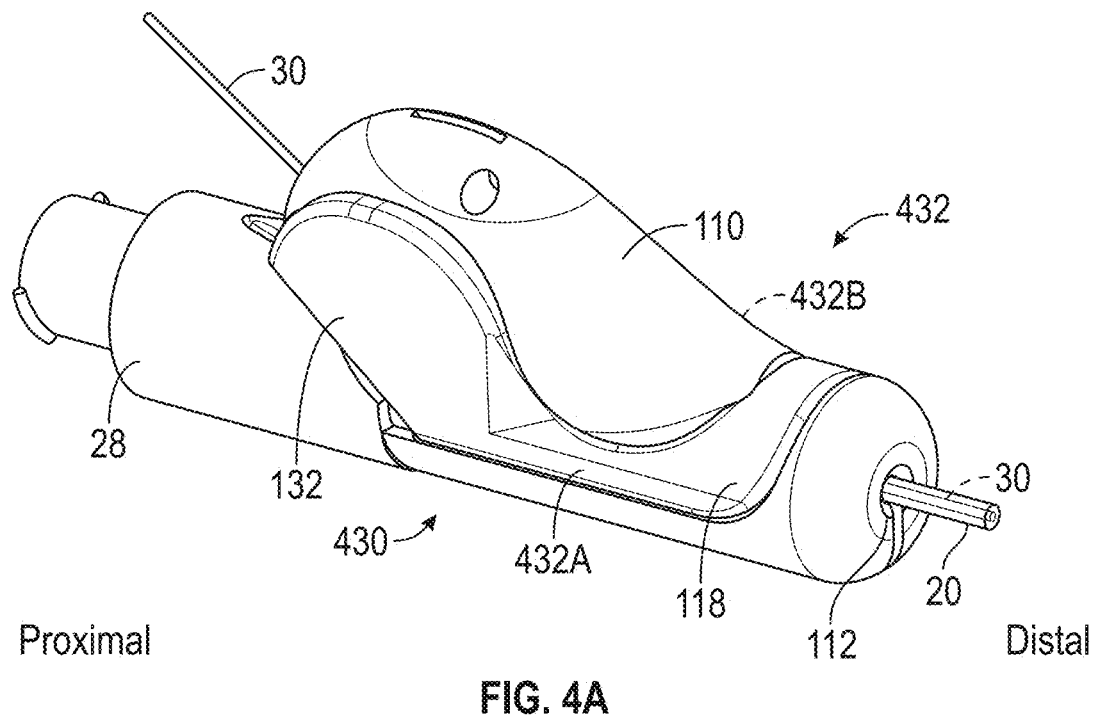
FIGS. 4A-4B show perspective views of a pinch-activated guidewire stabilization system, in accordance with embodiments disclosed herein.

In an embodiment, the pinch-activated stabilization system 430 can include a first lever 432A disposed on a first side of the housing 110 and a second lever 432B disposed on a second side of the housing 110, opposite the first lever 432A across a longitudinal axis. As shown in FIG. 4A, the first lever 432A and the second lever 432A can be arranged along a lateral axis. However, it will be appreciated that the first lever 432A and the second lever 432A can be arranged along other axes, such as a transverse axis or an axis extending at an angle therebetween. Advantageously, the pinch-activated guidewire stabilization system 430 can apply equal opposing forces to the guidewire 30 to mitigate bending or kinking of the guidewire 30, or deviating the guidewire 30 from a central axis, when in the locked position.

Figure 4B:
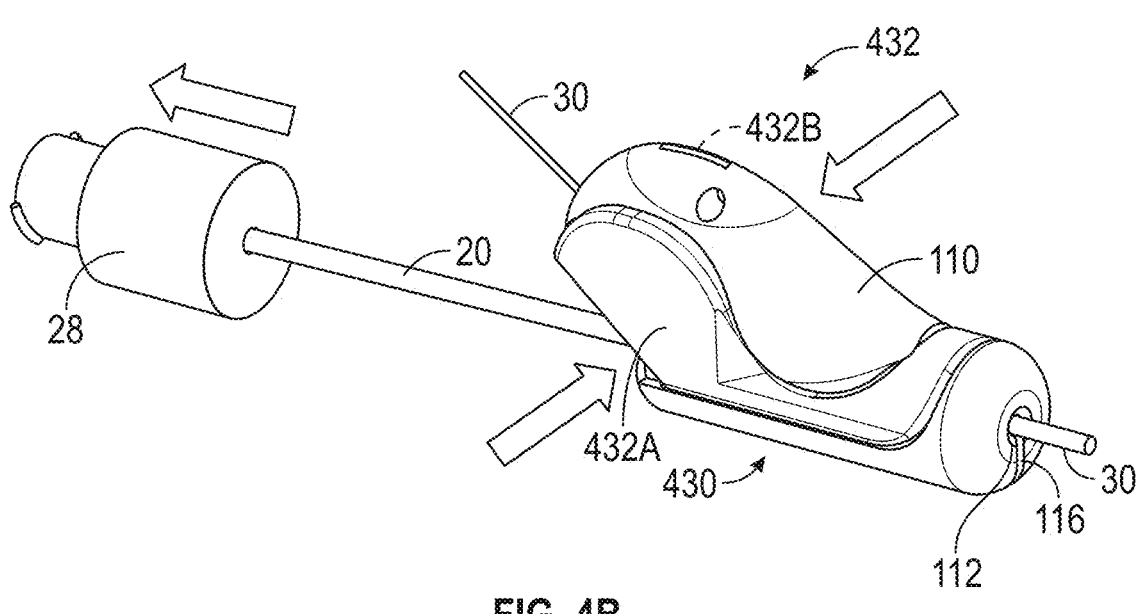
Figure 4C:
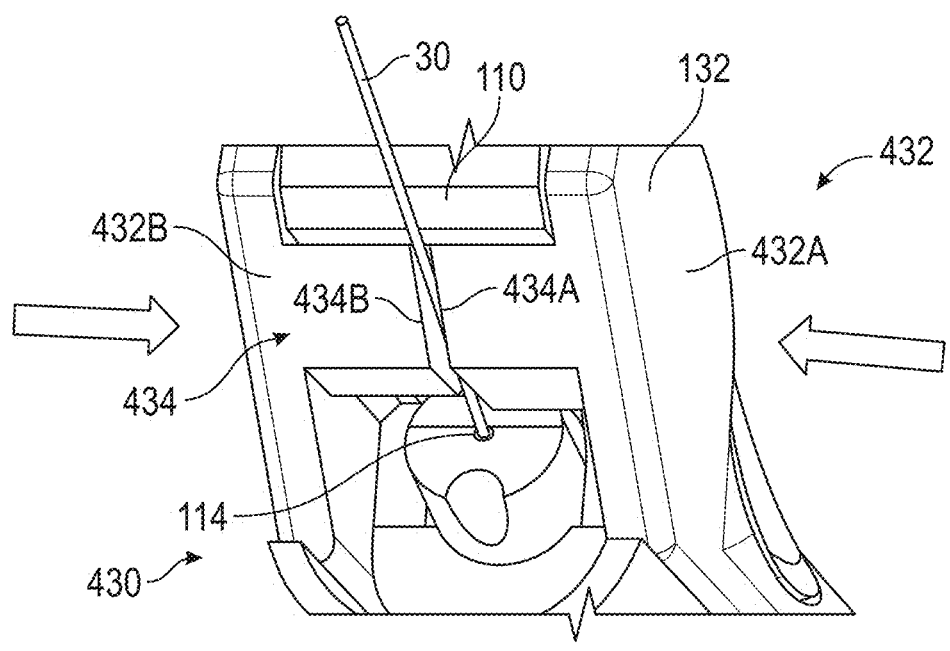
FIGS. 4C-4E show close up detail of the pinch-activated guidewire stabilization system of FIG. 4A, in accordance with embodiments disclosed herein.

In an embodiment, as shown in FIG. 4C, the lever 432 can include a gripping surface 434, for example, a first gripping surface 434A disposed on a first lever 432A, and a second gripping surface 434B disposed on the second lever 432B. In an embodiment, the gripping surface 434 can contact the guidewire 30 when the stabilization system 430 is in the locked position and can mitigate or inhibit movement of the guidewire 30 relative to the housing 110. In an embodiment, in the unlocked position, the gripping surface 434 can be in a spaced apart relationship from the guidewire 30 to allow the guidewire 30 to slide freely relative to the housing 110, e.g. through the guidewire channel 114.

In an embodiment, in the unlocked position, the gripping surface 434 can contact the guidewire 30 in an interference engagement to allow the guidewire 30 to slide relative to the housing 110, e.g. through the guidewire channel 114. However, friction between the gripping surface 434 and the guidewire 30 in the unlocked position can prevent the guidewire 30 from sliding freely. Worded differently, in the unlocked position a user can position the guidewire 30 in a first position relative to the housing 110 and the guidewire 30 can remain in the first position until repositioned to a second position without actuating the pinch-activated stabilization system 430. In an embodiment, the gripping surface 434 can be formed of the same material as the lever 432 and the housing 110, e.g. a first material. The first material can be a plastic, polymer, metal, alloy, composite, or the like and display substantially resilient, rigid, or high durometer mechanical properties. In an embodiment, the first material can display little or no elastic deformation when gripping the guidewire 30, as such, the pinch stabilization system 430 can provide increased pressure to the guidewire 30 in the locked position ensuring a secure grip.

Figure 4D:
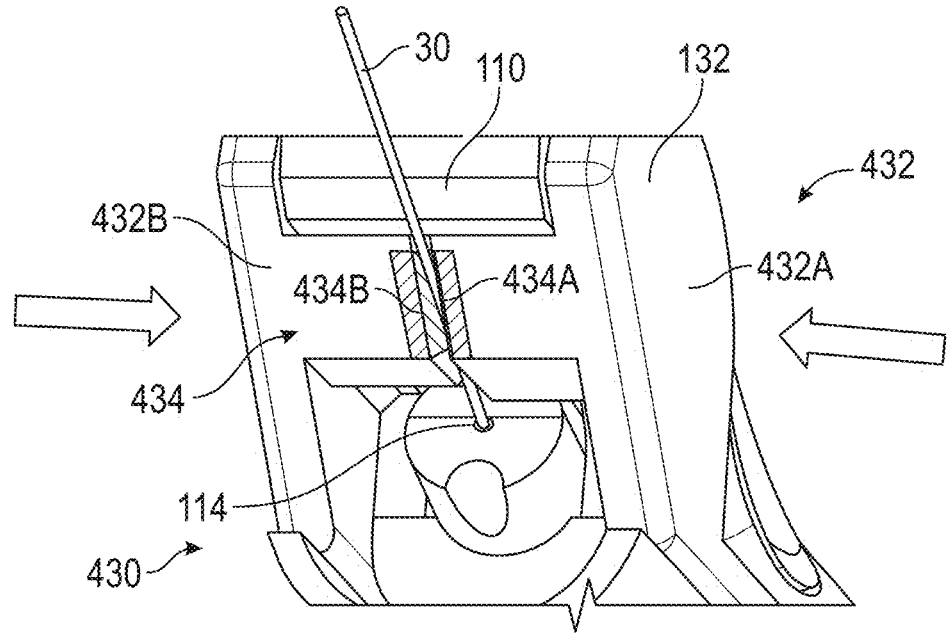

In an embodiment, as shown in FIG. 4D the gripping surface 434 can include a second material, different from a first material of the lever 432 or housing 110. The second material can include a high friction co-efficient, as described herein. In an embodiment, the second material can be more compliant, or of a lower durometer, than the first material and can elastically deform about the guidewire 30 when the stabilization system 430 is in the locked position. Advantageously, the gripping surface 434 including the second material can prevent kinking of the guidewire 30 when gripped by the pinch-activated stabilization system 430 and can provide an increased contact surface area between the gripping surface 434 and the guidewire 30.

Figure 4E:
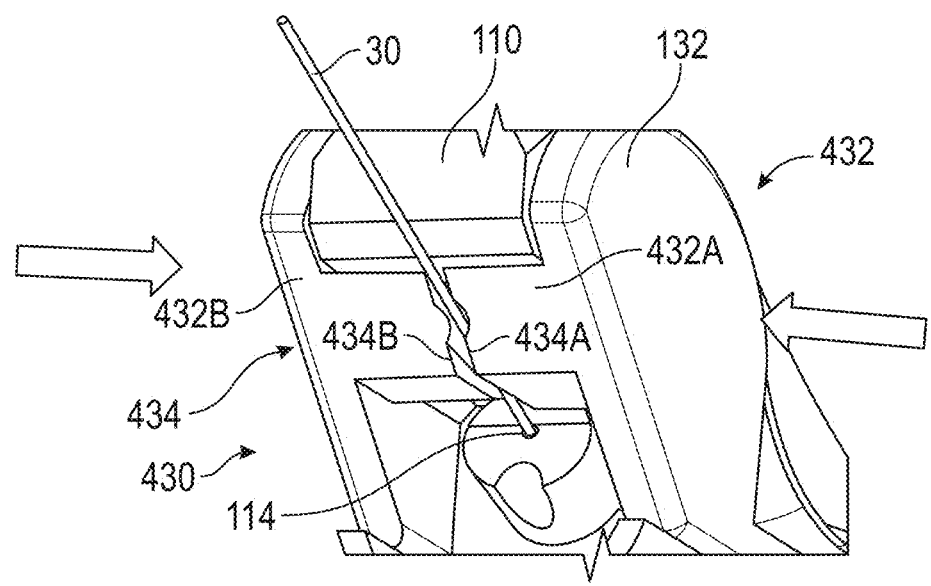

In an embodiment, as shown in FIG. 4E the gripping surface 434 can include a protrusion and/or detent. For example, the first gripping surface 434A can include a detent and the second gripping surface 434B can include a protrusion configured to engage the detent in the locked position. It will be appreciated, however, that other shapes, numbers and combinations of protrusions and detents are contemplated to fall within the scope of the present invention. In an embodiment, the guidewire 30 can be formed of a super-elastic material such as Nitinol or the like. In the locked position, the protrusion and detent can elastically deform the guidewire 30 between the first gripping surface 434A and the second gripping surface 434B to a non-linear shape and provide a secure grip on the guidewire 30. In the unlocked position, the guidewire 30 can resume the original linear shape. In an embodiment, a surface of the protrusion or detent can engage the guidewire 30 in the unlocked position, in an interference fit configured to prevent the guidewire 30 from sliding freely while also allowing a clinician to reposition the guidewire 30 relative to the housing 110, as described herein.

In an exemplary method of use, as shown in FIG. 4B, a clinician can apply opposing, "pinching" forces to the first lever 432A and the second lever 432B along an axis extending at an angle to an axis of the guidewire 30 to actuate the stabilization system 430 and grip the guidewire 30 between gripping surfaces 434A and 434B. In an embodiment, actuating the levers 432A, 432B, can cause the needle hub 28 to disengage the housing 110. The clinician can then retract the needle 20 proximally. The needle 20 can be removed leaving the guidewire 30 in position. Advantageously, the stabilization system 430 can allow a clinician to stabilize the housing 110, actuate the actuator button 132 and/or disengage the needle hub 28 from the housing 110, or combinations thereof, with a single hand or in a single action. In an embodiment, the housing 110 can include a housing slot 116 extending longitudinally and communicating between an outer surface of the housing 110, e.g. a bottom surface, and one or both of the needle channel 112 and the guidewire channel 114. Once the needle 20 has been removed, the clinician can release the stabilization mechanism 430 to release the guidewire 30 and disengage the housing 110 from the guidewire 30 by sliding a portion of the guidewire 30 through the housing slot 116.

Figure 5A:
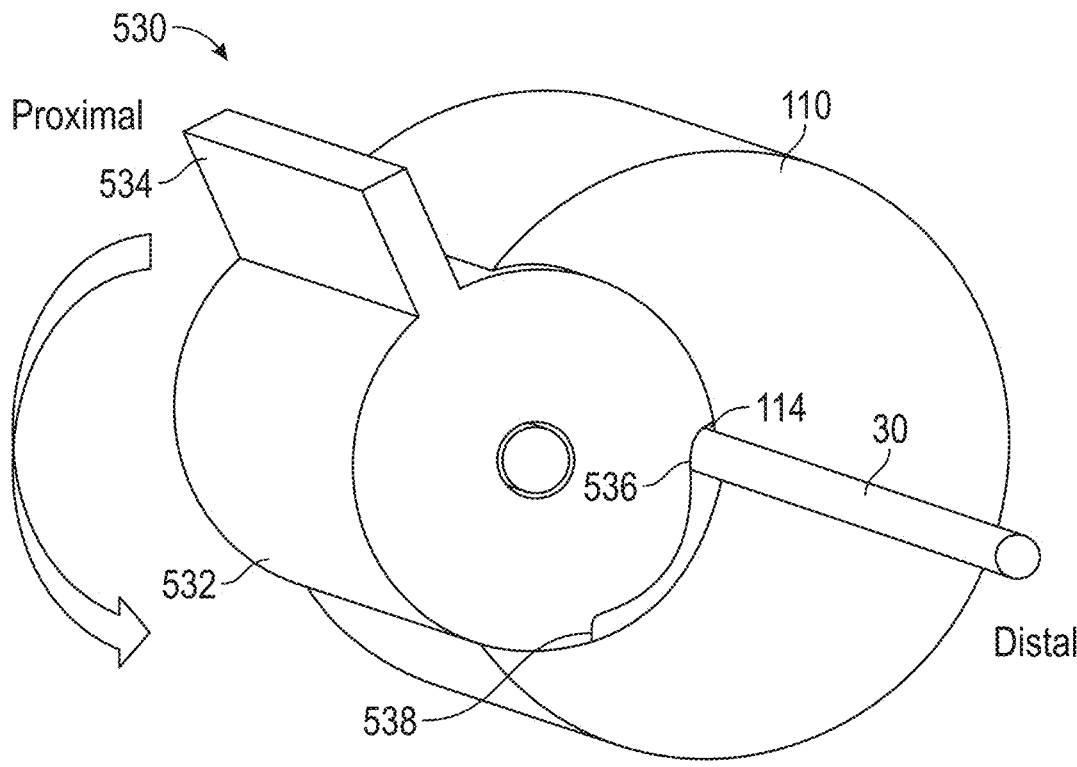
FIG. 5A shows a perspective view of a cam guidewire stabilization system, in accordance with embodiments disclosed herein.
Figure 5B:
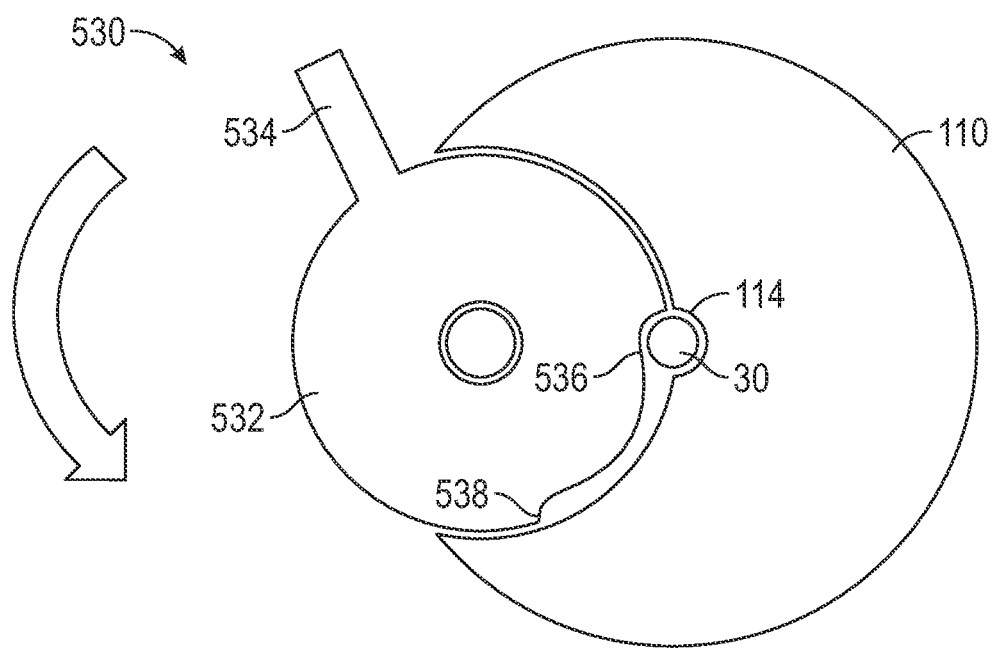
FIGS. 5B-5C show cross-section views of the cam guidewire stabilization system of FIG. 5A, in accordance with embodiments disclosed herein.
Figure 5C:
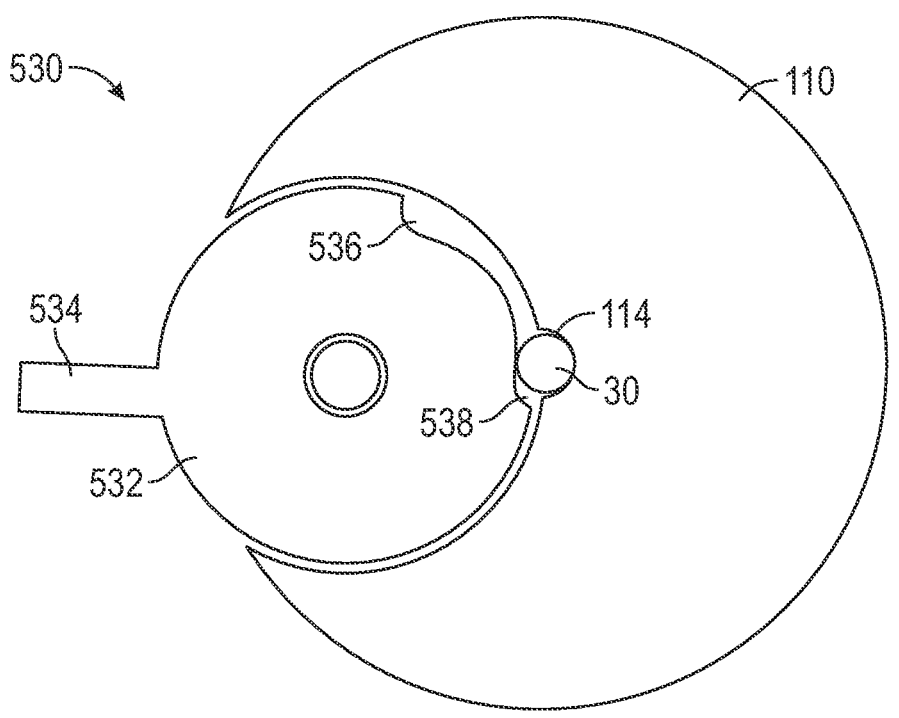

FIGS. 5A-5C show an embodiment of a cam guidewire stabilization system 530. In an embodiment, the cam stabilization system 530 can include a cam 532 rotatably engaged with the housing 110 between an unlocked position (FIG.

5A, 5B) and a locked position (FIG. 5C). In an embodiment, the cam 532 can rotate about an axis extending parallel to an axis of the guidewire 30. However, it will be appreciated that the cam 532 can rotate about an axis extending at an angle relative to the axis of the guidewire 30. In an embodiment, the cam 532 can be stable in one or both of the locked position and the unlocked position. In an embodiment, the cam 532 can include a cam lever 534 extending therefrom and configured to provide mechanical advantage to rotate the cam 532. Further, the position of the cam lever 534 relative to the housing 110 can indicate to a user if the cam is in the locked or unlocked position. In an embodiment, the lever 534 can include one or more symbols, colors, alpha-numeric symbols or the like configured to indicate to a user if the cam 532 is in the locked or unlocked position.

In an embodiment, the cam 532 can include a first notch 536 and a second notch 538, each extending through the cam 532 along a longitudinal axis, i.e. an axis that extends parallel to the axis of the guidewire 30 or guidewire channel 114. In the unlocked position, the first notch 536 can align with the guidewire channel 114 and guidewire 30 (FIG. 5B). In the locked position, the second notch 538 can align with the guidewire channel 114 and guidewire 30 (FIG. 5C).

In an embodiment, the first notch 536 can define a larger diameter than the second notch 538. In the unlocked position, the first notch 536 can co-operate with the housing 110 to define a portion of the guidewire channel 114. In an embodiment, the first notch 536 and housing 110 can define a portion of the guidewire channel 114 having an inner diameter that is larger than an outer diameter of the guidewire 30. As such, in the unlocked position, the guidewire 30 can slidably engage the first notch 536. In the locked position, the second notch 538 can co-operate with the housing 110 to define a portion of the guidewire channel 114. In the locked position, a surface of the second notch 528 can compress the guidewire 30 against a surface of the housing 110 to grip the guidewire 30 and prevent axial movement thereof. As will be appreciated, although the cam stabilization system 530 can transition between the locked position and the unlocked position, i.e. between the first notch 536 and the second notch 538, through a rotational movement as shown, other paths of motion, such as linear, elliptical, or multi-directional movements, or axes of rotation, or combinations thereof, are also contemplated to fall within the scope of the present invention.

Figure 6A:
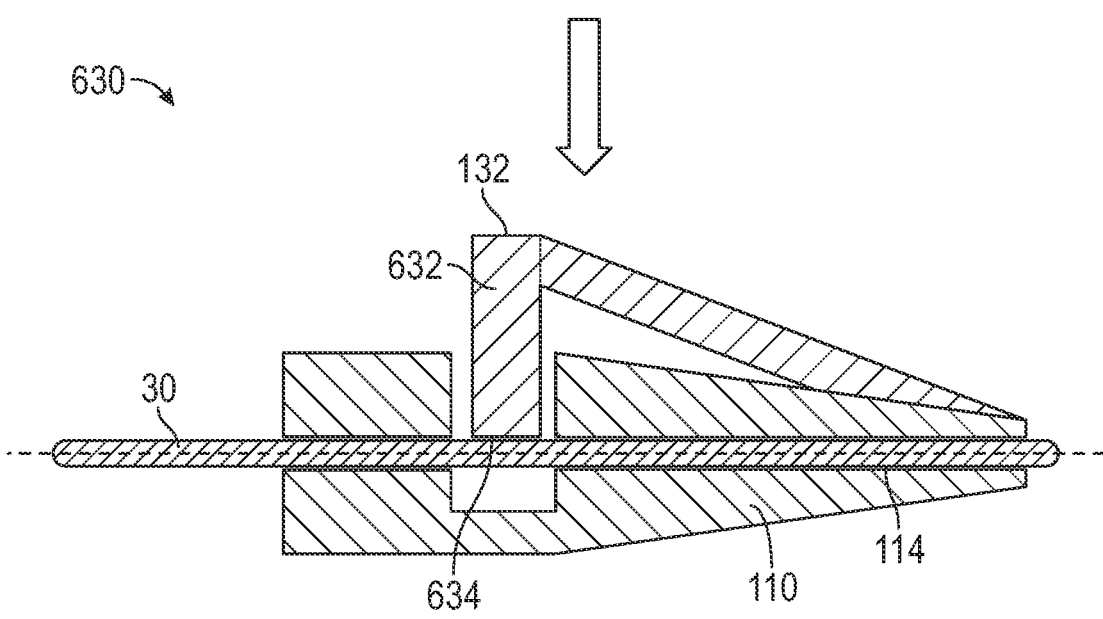
FIGS. 6A-6B show longitudinal cross-section views of a crimp guidewire stabilization system, in accordance with embodiments disclosed herein.
Figure 6B:
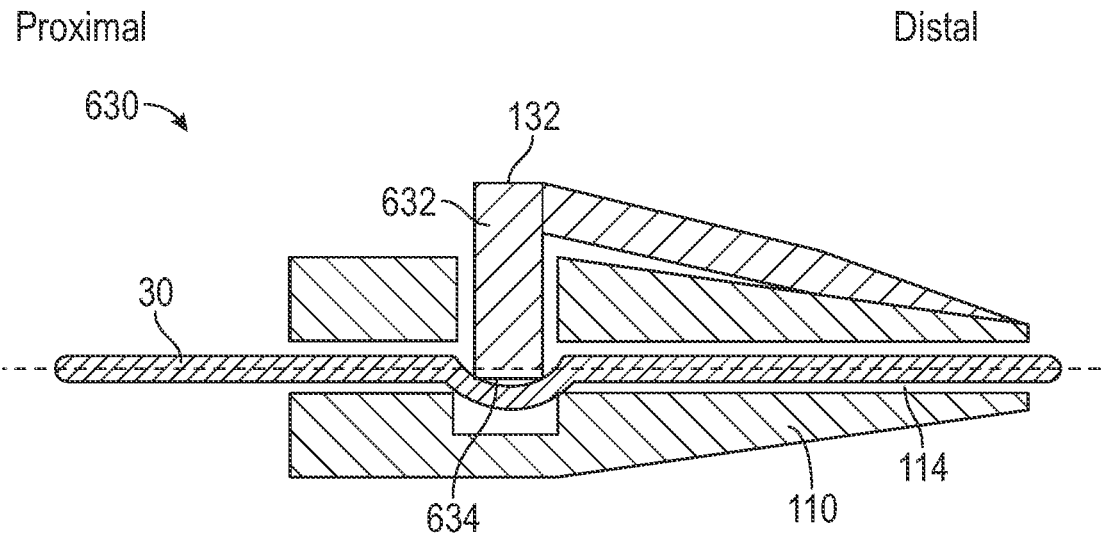

FIGS. 6A-6B show an embodiment of a crimping stabilization mechanism 630 and can include a crimp lever 632 hingedly coupled to the housing 110 and transitionable between an unlocked position (FIG. 6A) and a locked position (FIG. 6B). In an embodiment, the lever 632 can be biased towards the unlocked position. In an embodiment, an outer surface of the lever 632 can define an actuation button 132. In an embodiment, an inner surface of the lever 632 can define a gripping surface 634 configured to engage the guidewire 30.

In use, a clinician can apply a force to the actuation button 132 and slide the gripping surface 634 radially inward relative to an axis of the guidewire. In an embodiment, the gripping surface 634 can extend into the guidewire channel 114. In an embodiment, the gripping surface 634 can impinge on the guidewire 30 and deflect a linear portion of the guidewire 30 from a central axis of the guidewire 30, to crimp the portion of the guidewire 30 to a non-linear configuration and inhibit axial movement thereof. The clinician can release the actuation button 132 and allow the lever 632 to transition back to the unlocked position. The guidewire 30 can return to the uncrimped, linear shape and can slide relative to the housing 110. In an embodiment, a non-linear configuration can include bending, kinking, crimping, twisting, or forcing the guidewire 30 into a tortuous path, or combinations thereof. Advantageously, the crimping stabilization mechanism 630 can secure the guidewire 30 even when the guidewire 30 includes a coating or similar lubricant disposed on a surface thereof.

Figure 7A:
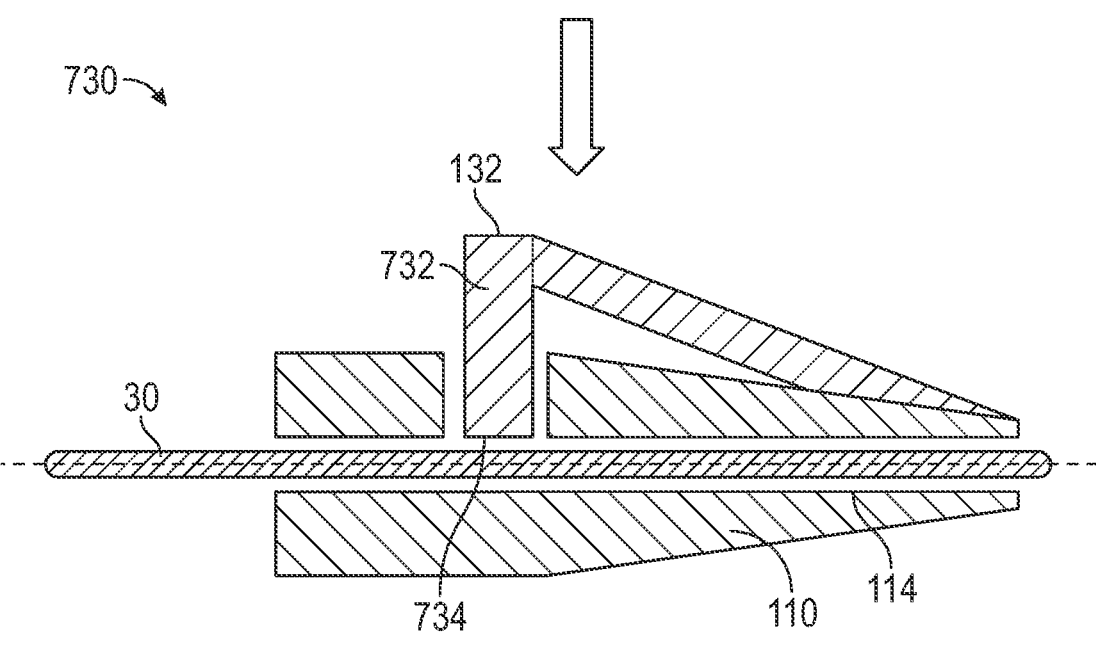
FIGS. 7A-7B show longitudinal cross-section views of a compression guidewire stabilization system, in accordance with embodiments disclosed herein.
Figure 7B:
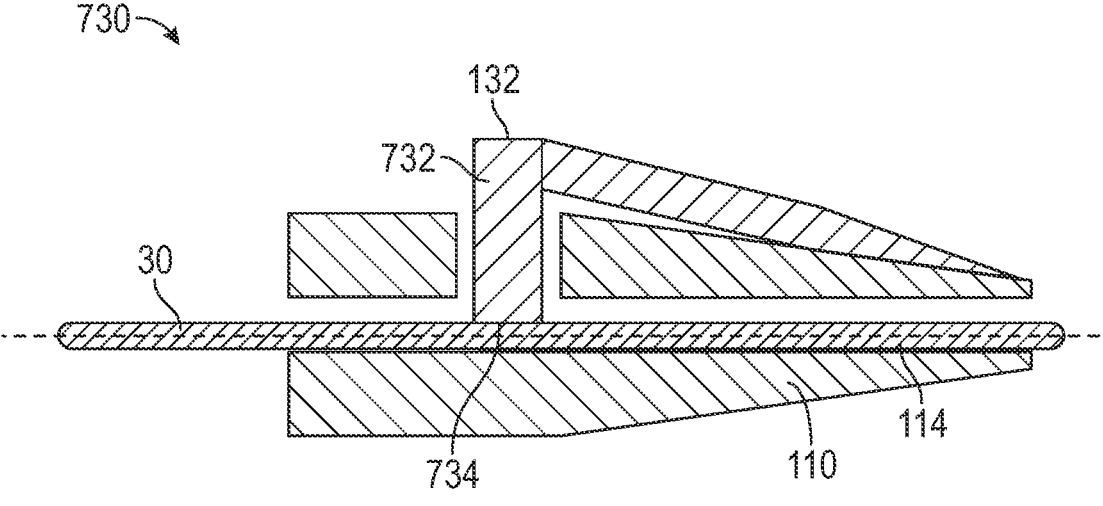

FIGS. 7A-7B show an embodiment, of a compression stabilization mechanism 730 and can include a single lever 732 hingedly coupled to the housing 110 and transitionable between an unlocked position (FIG. 7A) and a locked position (FIG. 7B). In an embodiment, the lever 732 can be biased towards the unlocked position. In an embodiment, an outer surface of the lever 732 can define an actuation button 132. In an embodiment, an inner surface of the lever 732 can define a gripping surface 734 configured to engage the guidewire 30.

In use, a clinician can apply a force to the actuation button 132 and slide the gripping surface 734 radially inward relative to an axis of the guidewire 30. In an embodiment, the gripping surface 734 can extend into the guidewire channel 114. In an embodiment, the gripping surface 734 can impinge on a portion of the guidewire 30 and can compress the portion of the guidewire 30 against an opposite wall of the guidewire channel 114. In an embodiment, the compression stabilization mechanism 730 can inhibit axial movement of the guidewire 30 relative to the housing 110 without bending or kinking the guidewire 30, i.e. maintaining a substantially linear configuration of the guidewire 30 in the locked position. The lever 732 compressing the portion of the guidewire 30 can prevent the guidewire 30 from sliding axially relative to the housing 110. The clinician can release the actuation button 132 and allow the lever 732 to transition back to the unlocked position. The guidewire 30 can then slide relative to the housing 110.

Figure 8A:
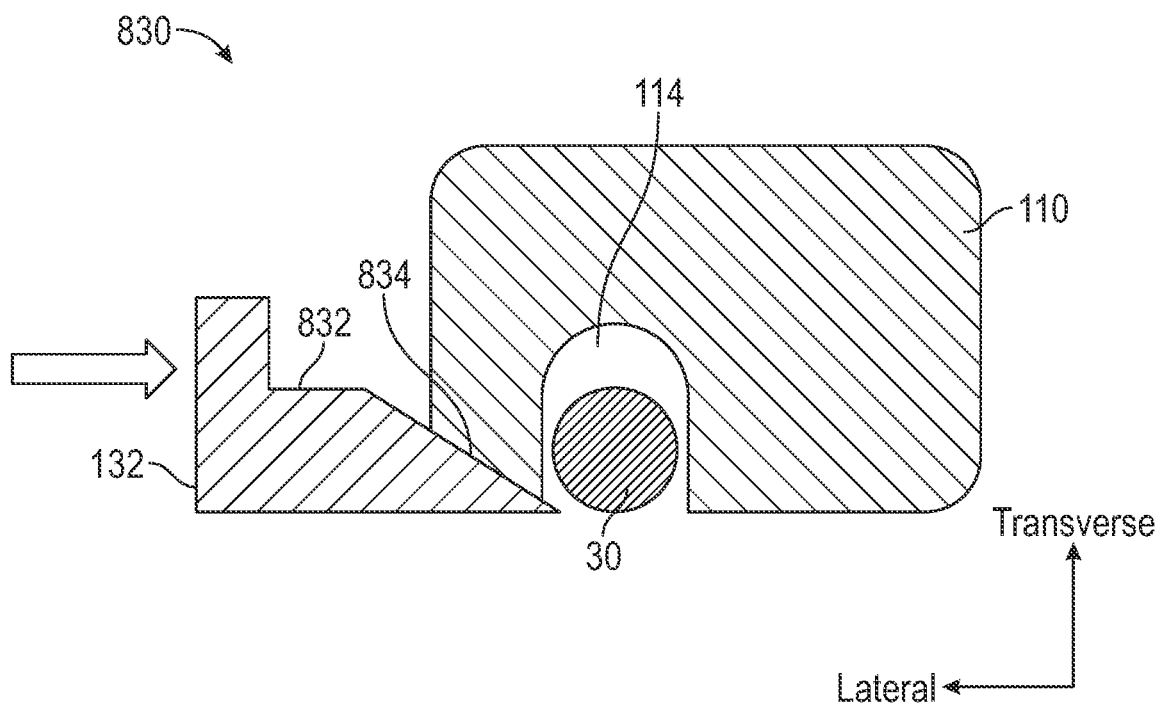
FIGS. 8A-8B show lateral cross-section views of a clamp guidewire stabilization system, in accordance with embodiments disclosed herein.
Figure 8B:
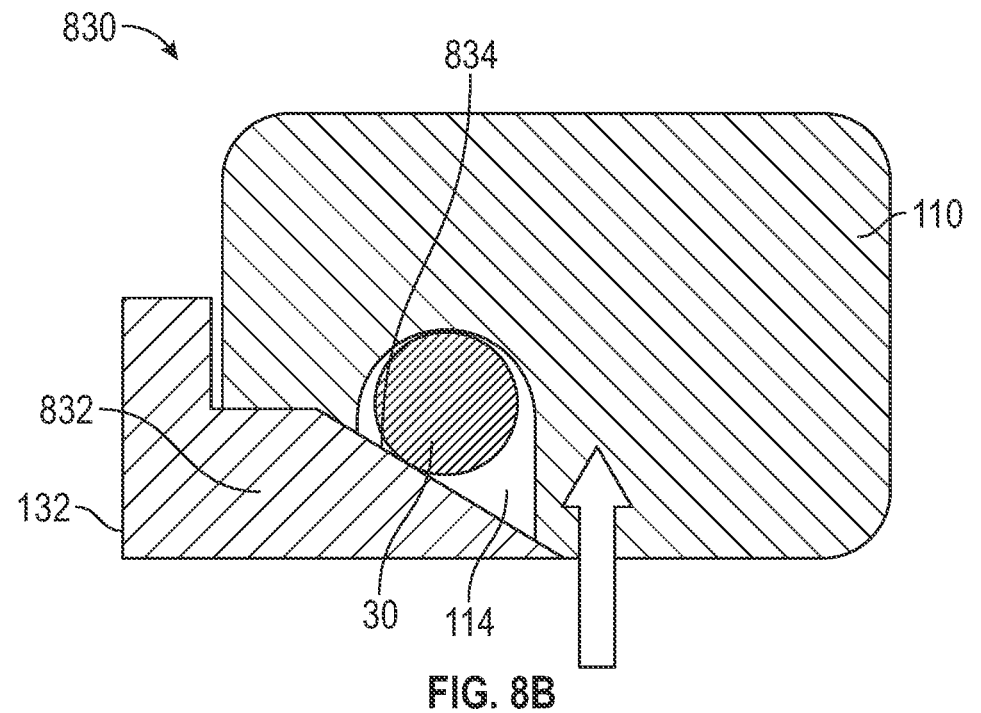

FIGS. 8A-8B show an embodiment of a clamp stabilization mechanism 830 and can include a clamp arm 832 slidably engaged with the housing 110 along a first axis, for example an axis extending at an angle relative to an axis of the guidewire channel 114. In an embodiment, the guidewire 30 can extend substantially longitudinally, and the clamp arm 832 can slidably engage the housing 110 substantially along a lateral axis. The clamp arm 832 can be transitionable between an unlocked position (FIG. 8A) and a locked position (FIG. 8B). In an embodiment, the clamp arm 832 can include a biasing member and can be biased towards the unlocked position. In an embodiment, an outer surface of the clamp arm 832 can define an actuation button 132. In an embodiment, an inner surface of the clamp arm 832 can define a gripping surface 834 configured to engage the guidewire 30. In an embodiment, the gripping surface 834 can be angled relative to the first axis, e.g. relative to the lateral axis, to provide a wedge shaped cross-sectional profile.

In use, a clinician can apply a force to the actuation button 132 urging the clamp arm 832 along a first axis, substantially perpendicular to the longitudinal axis, into the housing 110. In an embodiment, the gripping surface 734 can extend into the guidewire channel 114. The wedge-shaped gripping surface 834 can urge a portion of the guidewire 30 along a third axis, e.g. a transverse axis, extending at an angle relative to both the first axis of the clamp arm (lateral axis) and the second axis of the guidewire 30 (longitudinal). The gripping surface can urge the portion of the guidewire 30 against a wall of the guidewire channel 114, clamping the guidewire 30 thereto and preventing axial movement of the guidewire 30 relative to the housing 110. The clinician can release the actuation button 132 and allow the clamp arm 832 to transition back to the unlocked position, releasing the guidewire 30 and allowing the guidewire 30 to slide relative to the housing 110.

Figure 9A:
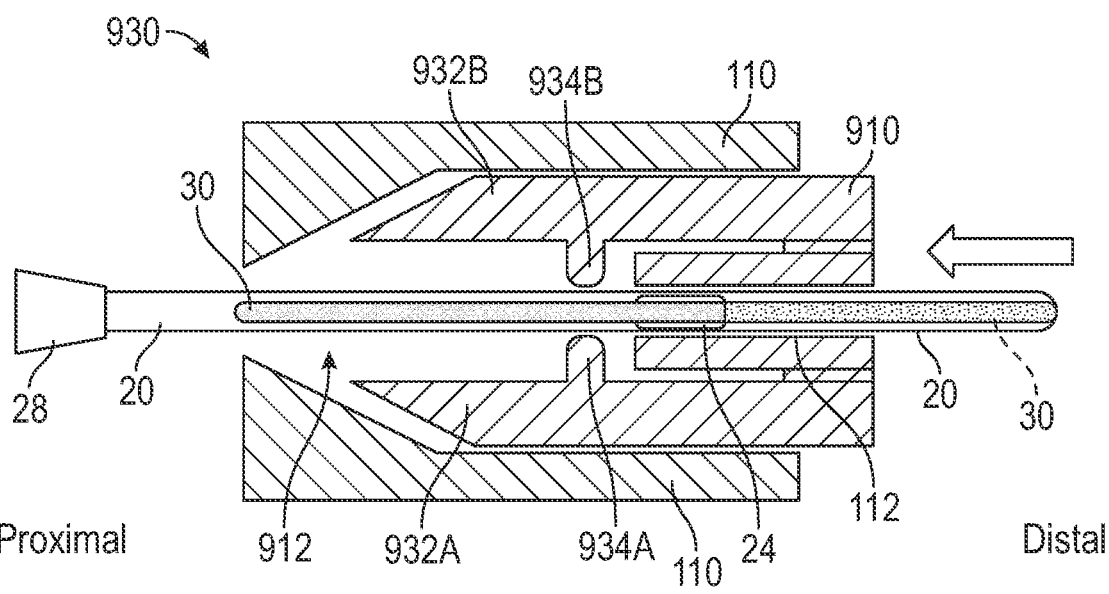
FIGS. 9A-9B show plan, cross-section views of a needle-activated guidewire stabilization system, in accordance with embodiments disclosed herein.
Figure 9B:
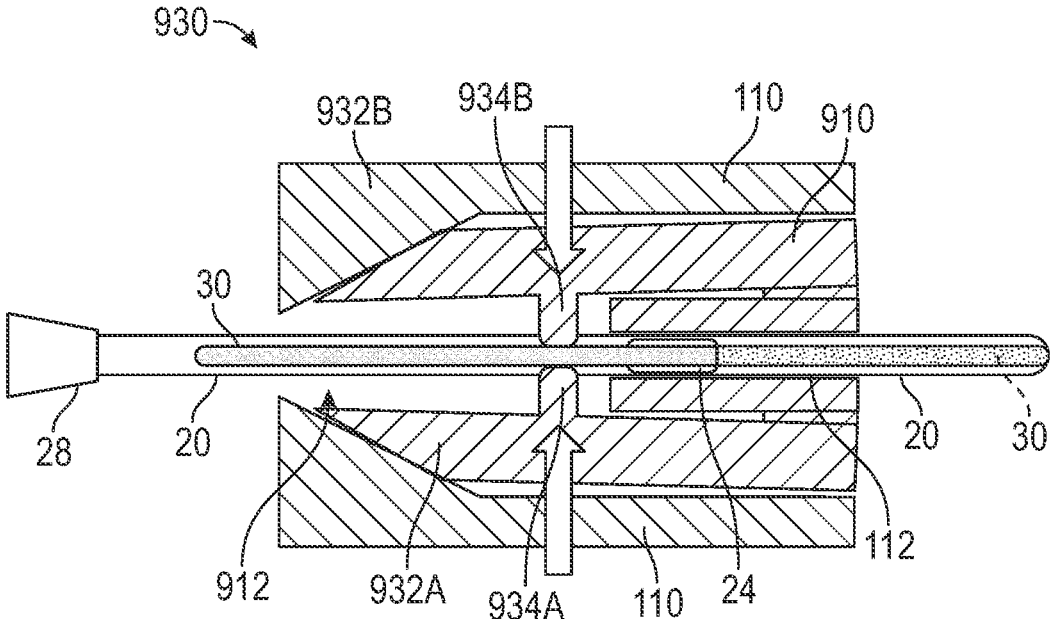

FIGS. 9A-9B show an embodiment of a needle-activated stabilization mechanism 930. In an embodiment, a clinician can detach the needle hub 28 from the housing 110 and withdraw the needle 20 from the needle channel 112. As the needle 20 is withdrawn proximally, the needle 20 can engage an inner needle housing 910 and can transition the needle activated stabilization mechanism 930 to the locked position. Once the needle 20 has fully disengaged the housing 110, the inner housing 910 can transition back to the unlocked position, releasing the guidewire 30 and allowing the housing 110 to disengage the guidewire 30.

In an embodiment, the needle activated stabilization mechanism 930 can include an inner housing 910, slidably engaged with the housing 110, e.g. an outer housing 110. The outer housing 110 can define a channel 912 configured to receive the inner housing 910 therein and defining a tapered proximal end. The inner housing 910 can define a portion of the needle channel 112 and can include a first arm 932A and a second arm 932B. The inner housing 910 can be formed of a resilient material. As such the first arm 932A and a second arm 932B can be flexible, and elastically deform radially inward from an unlocked position (FIG. 9A) to a locked position (FIG. 9B). Each arm 932 can define a gripping surface 934, for example a first gripping surface 934A and a second gripping surface 934B. Further a proximal end of the arm 932 can define a tapered surface configured to engage the tapered proximal end of the outer housing 110.

In an embodiment, a portion of the inner housing 910, defining the portion of the needle channel 112, can engage the needle 20 in an interference fit. As such, as the needle 20 is urged proximally through the needle channel 112, the inner housing 910 can engage the needle 20 and can be urged proximally. The tapered proximal end of the inner housing 910 can engage the tapered proximal end of the housing channel 912 and can deflect the arms 932 radially inward such that the gripping surface 934 can engage a portion of the guidewire 30 extending from the guidewire aperture 24 of the needle 20, preventing axial movement of the guidewire 30 relative to the outer housing 110. The needle 20 can continue to be urged proximally, urging a portion of the guidewire 30 through the needle slot 26, as described herein. When the needle 20 has been removed from the outer housing 110, the inner housing 910 is free to move distally, disengaging the proximal end of the housing channel 912 and allowing the arms 932 to return to the undeflected, unlocked position, and releasing the guidewire 30.

As shown in FIGS. 9A-9B, the needle-activated stabilization mechanism 930 can be activated by a linear movement of the needle 20 relative to the housing 110. In an embodiment, the needle activated stabilization mechanism 930 can also be activated by other axes or directions of movement of the needle such as rotational, helical, multidirectional, lateral, transverse, or perpendicular to the longitudinal axis, or combinations thereof, and are contemplated to fall within the scope of the present invention.

Figure 10A:
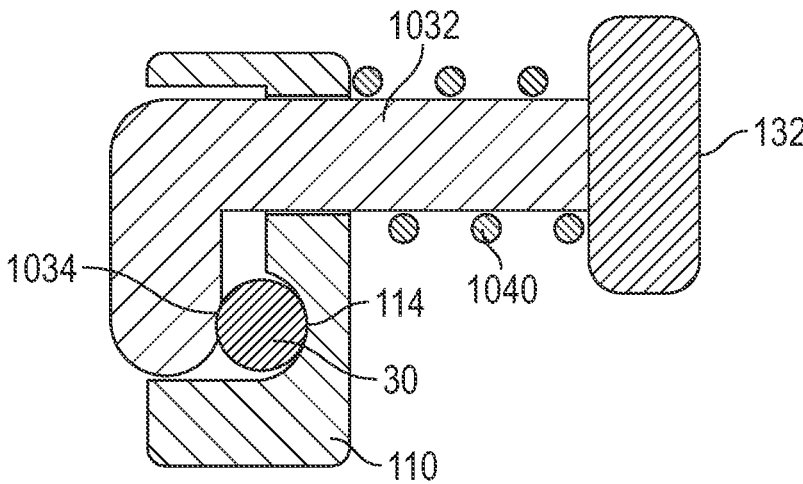
FIGS. 10A-10B show lateral cross-section views of a spring-activated guidewire stabilization system, in accordance with embodiments disclosed herein.
Figure 10B:
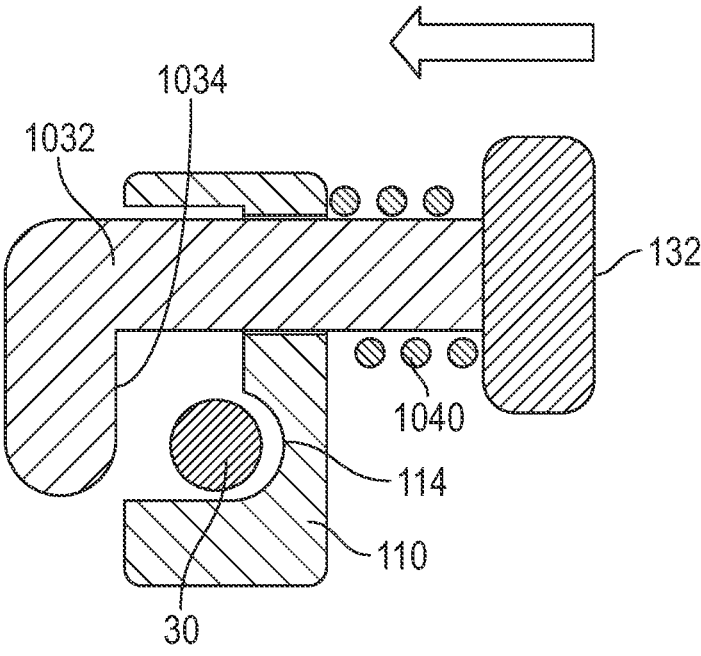

As shown in FIGS. 10A-10B, a spring-activated stabilization system 1030 can include a clamp arm 1032 slidably engaged with the housing 110 between a locked position and an unlocked position, along an axis extending at an angle relative to an axis of the guidewire 30. In an embodiment, the clamp arm 1032 can slidably engage the housing 110 along a lateral axis. An outer surface of the clamp arm 1032 can define an actuator button 132. An inner surface of the clamp arm 1032 can define a gripping surface 1034. In an embodiment, the spring-activated stabilization system 1030 can be biased towards the locked position. For example, the spring-activated stabilization system 1030 can include a compression spring 1040 disposed between the housing 110 and a surface of the clamp arm 1032 and configured to bias the clamp arm 1032 towards the locked position. It will be appreciated that other types and configurations of biasing member 1040 are contemplated to fall within the scope of the present invention. In the locked position the gripping surface 1034 can impinge against the guidewire and compress a portion of the guidewire 30 against a wall of the guidewire channel 114. In the unlocked position, the gripping surface 1034 can disengage the guidewire 30 and allow the guidewire 30 to slide axially.

In use, the spring-activated stabilization system 1030 can engage the guidewire 30 and lock the position of the guidewire 30 relative to the housing 110. Once the vasculature has been accessed, a clinician can apply a force to the actuation button 132 to overcome the force of the biasing member 1040 and transition the clamp arm 1032 from the locked position to the unlocked position. The clinician can advance the guidewire 30 to a target location and then release the actuator button 132 to let the biasing member 1040 transition the clamp arm 1032 to the locked position. Advantageously, the clinician can then stabilize the housing 110 without having to maintain pressure on the button 132, while the needle 20 is withdrawn proximally, as described herein.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement system, comprising:
a needle extending along a longitudinal axis and supported by a needle hub, the needle defining a needle lumen and including an aperture extending through a wall of the needle adjacent the needle hub, and a slot extending from the aperture to a distal tip of the needle;
a guidewire having a distal tip extending through the aperture and into the needle lumen; and
a guidewire stabilization system, comprising:
a housing coupled to the needle hub and defining a needle channel having a portion of the needle disposed therethrough; and
a stabilization mechanism transitionable between a locked position and an unlocked position, the stabilization mechanism configured to grip a portion of the guidewire in the locked position to stabilize the guidewire relative to the housing as the needle is withdrawn proximally from the needle channel of the housing.

2. The catheter placement system according to claim 1, wherein the stabilization mechanism is biased towards the unlocked position and includes an actuator button configured to be actuated and transition the stabilization mechanism from the unlocked position to the locked position.

3. The catheter placement system according to claim 2, wherein the actuator button is further configured to disengage the needle hub from the housing.

4. The catheter placement system according to claim 1, wherein the stabilization mechanism further includes a first lever and a second lever each pivotably coupled to the housing, the first lever defining a first actuator button and the second lever defining a second actuator button.

5. The catheter placement system according to claim 4, wherein a first gripping surface of the first lever and a second gripping surface of the second lever contact the guidewire in the locked position and inhibit axial movement thereof.

6. The catheter placement system according to claim 5, wherein one or both of the first gripping surface and the second gripping surface are in a spaced apart relationship from the guidewire in the unlocked position.

7. The catheter placement system according to claim 5, wherein one or both of the first gripping surface and the second gripping surface engage the guidewire in the unlocked position to allow the guidewire to slide axially from a first position to a second position and to maintain the guidewire in the second position until repositioned.

8. The catheter placement system according to claim 4, wherein one or both of the first lever and the second lever include a first material, and a gripping surface includes a second material, different from the first material and including a high frictional co-efficient relative to the first material.

9. The catheter placement system according to claim 8, wherein the second material includes one of a plastic, a polymer, an elastomer, a rubber, or a silicone rubber.

10. The catheter placement system according to claim 5, wherein the first gripping surface includes one of a first protrusion or a first detent configured to engage one of a second protrusion or a second detent disposed on the second gripping surface.

11. The catheter placement system according to claim 1, wherein the stabilization mechanism includes a first lever, hingedly coupled to the housing and defining a gripping surface configured to extend into a guidewire channel of the housing and impinge on the guidewire in the locked position.

12. The catheter placement system according to claim 11, wherein the gripping surface is configured to deflect the portion of the guidewire from a linear configuration to a non-linear configuration in the locked position to inhibit axial movement of the guidewire.

13. The catheter placement system according to claim 11, wherein the gripping surface is configured to compress the portion of the guidewire against a wall of the guidewire channel to inhibit axial movement of the guidewire in the locked position.

14. The catheter placement system according to claim 1, wherein the stabilization mechanism includes a clamp having a gripping surface and slidably engaged with the housing between the locked position and the unlocked position along a first axis extending perpendicular to a second axis of the guidewire, the gripping surface angled relative to the first axis.

15. The catheter placement system according to claim 14, wherein the gripping surface engages the portion of the guidewire in the locked position and compresses the portion of the guidewire against a wall of a guidewire channel along a third axis extending at an angle to both the first axis and the second axis.

16. The catheter placement system according to claim 1, wherein the stabilization mechanism includes a cam rotatable between the locked position and the unlocked position, the cam including a first notch that aligns with a guidewire channel in the unlocked position and a second notch that aligns with the guidewire channel in the locked position, the second notch configured to compress the portion of the guidewire against a wall of a guidewire channel to inhibit axial movement of the guidewire in the locked position.

17. The catheter placement system according to claim 16, wherein the cam is bistable in both the locked position and the unlocked position.

18. The catheter placement system according to claim 16, wherein the cam further includes a lever extending therefrom and configured to indicate to a user that the cam is in one of the locked position or the unlocked position.

19. The catheter placement system according to claim 1, wherein the stabilization mechanism further includes an inner housing, slidably engaged with a housing channel of the housing and configured to be urged proximally as the needle is withdrawn, and deflect an arm of the inner housing from the unlocked position to the locked position to inhibit axial movement of the guidewire.

20. The catheter placement system according to claim 19, wherein the inner housing defines a portion of the needle channel and is configured to slidably engage the needle in an interference fit engagement to urge the inner housing proximally as the needle is withdrawn from the needle channel.

21. The catheter placement system according to claim 19, wherein the inner housing further includes a tapered proximal end configured to engage a tapered proximal end of the housing channel and deflect the arm to the locked position as the needle is withdrawn from the needle channel.

22. The catheter placement system according to claim 19, wherein the inner housing includes a first arm defining a first gripping surface and a second arm defining a second gripping surface disposed opposite the first gripping surface across an axis of the guidewire, the first arm and the second arm configured to deflect inwards to grip the portion of the guidewire therebetween in the locked position.

23. The catheter placement system according to claim 1, wherein the stabilization mechanism is biased towards the locked position and includes an actuator button configured to transition a gripping surface of the stabilization mechanism from the locked position to the unlocked position.

24. The catheter placement system according to claim 23, further including a clamp arm slidably engaged with the housing between the locked position and the unlocked position, a first surface of the clamp arm defining the actuator button and a second surface of the clamp arm defining the gripping surface and configured to compress the portion of the guidewire against a wall of a guidewire channel to inhibit axial movement of the guidewire in the locked position.

25. The catheter placement system according to claim 24, further including a compression spring configured to bias the clamp arm to the locked position.

* * * * *